(12) United States Patent
Semrau et al.

(10) Patent No.: US 8,629,239 B2
(45) Date of Patent: Jan. 14, 2014

(54) *METHYLOCYSTIS* STRAIN SB2 MATERIALS AND METHODS

(75) Inventors: Jeremy D. Semrau, Ann Arbor, MI (US); Warren Gallagher, Eau Claire, WI (US); Sukhwan Yoon, Ann Arbor, MI (US); Jeongdae Im, Ann Arbor, MI (US); Alan A. DiSpirito, Ames, IA (US); Sung-Woo Lee, Hillsboro, OR (US); Scott Hartsel, Eau Claire, WI (US); Marcus T. McEllistrem, Eau Claire, WI (US)

(73) Assignees: Iowa State University Research Foundation, Inc., Ames, IA (US); The Regents of the University of Michigan, Ann Arbor, MI (US); WiSys Technology Foundation, Madison, WI (US)

( * ) Notice: Subject to any disclaimer, the term of this patent is extended or adjusted under 35 U.S.C. 154(b) by 0 days.

(21) Appl. No.: 13/198,669

(22) Filed: Aug. 4, 2011

(65) Prior Publication Data

US 2012/0034594 A1 Feb. 9, 2012

Related U.S. Application Data

(60) Provisional application No. 61/371,447, filed on Aug. 6, 2010.

(51) Int. Cl.
*C07K 4/04* (2006.01)
*C07K 7/54* (2006.01)
(52) U.S. Cl.
USPC .......................... 530/300; 530/400; 530/506
(58) Field of Classification Search
None
See application file for complete search history.

(56) References Cited

PUBLICATIONS

Behling, et al., NMR, Mass Spectrometry and Chemical Evidence Reveal a Different Chemical Structure for Methanobactin That Contains Oxazolone Rings, Journal of the American Chemical Society, 130: 12604-12605, 2008.*
DiSpirito, et al., Copper-Binding Compounds from *Methylosinus trichosporium* OB3b, Journal of Bacteriology, 180(14): 3606-3613, 1998.*
Choi, et al., Spectral and thermodynamic properties of Ag(I), Au(III), Cd(II), Co(II), Fe(III), Hg(II), Mn(II), Ni(II), Pb(II), U(IV), and Zn(II) binding by methanobactin from *Methylosinus trichosporium* OB3b, Journal of Inorganic Biochemistry 100: 2150-2161, 2006.*
Auman, et al. (2001) nifH sequences and nitrogen fixation in type I and type II methanotrophs. Appl. Environ. Microbiol. 67: 4009-4016.
Auman, et al. (2000) Molecular characterization of methanotrophic isolates from freshwater lake sediment. Appl Environ Microbiol 66: 5259-5266.
Axe, et al. (1995) Transport of lactate and acetate through the energized cytoplasmic membrane of *Escherichia coli*. Biotechnol Bioeng 47: 8-19.
Belova, et al. (2010) Acetate utilization as a survival strategy of peat-inhabiting *Methylocystis* . Environ Microbiol Rep. DOI: 10.1111/j.1758-2229.2010.00180.x.
Best, et al. (1981) Methane oxidizing activity and membrane morphology in methanol grown obligate methanotroph, *Methylosinus trichosporium* OB3b. J Gen Microbiol 125:73-84.
Bowman, et al. (1993) Revised taxonomy of the methanotrophs—description of Methylobacter gen-nov, emendation of *Methylococcus*, validation of *Methylosinus* and *Methylocystis* species, and a proposal that the family Methylococcaceae includes only the group-I methanotrophs. Intl J Syst Bacteriol 43: 735-753.
Brusseau, et al. (1990) Optimization of trichloroethylene oxidation by methanotrophs and the use of a colorimetric assay to detect soluble methane monooxygenase activity. Biodegradation 1: 19-29.
Cashion, et al. (1977) A rapid method for the base ratio determination of bacterial DNA. Anal Biochem 81: 461-466.
Choi, et al. (2003) The membrane-associated methane monooxygenase (pMMO) and pMMO-NADH: quinone oxidoreductase complex from *Methylococcus capsulatus* Bath. J Bacteriol 185: 5755-5764.
Cornish, et al. (1984) In vivo 13C NMR investigations of methanol oxidation by the obligate methanotroph *Methylosinus trichosporium* OB3b. J Gen Microbiol 130: 2564-2575.
Costello, et al. (1999) Molecular characterization of functional and phylogenetic genes from natural populations of methanotrophs in lake sediments. Appl Environ Microbiol 65: 5066-5074.
Dedysh, et al. (2000) *Methylocella palustris* gen nov., sp. nov. a new methane-oxidizing acidophilic bacterium from peat bogs, representing a novel subtype of serine pathway methanotrophs. Int J Syst Evol Microbiol 50: 955-969.
Dedysh, et al. (2005) *Methylocella* species are facultatively methanotrophic. J Bacteriol 187: 4665-4670.

(Continued)

*Primary Examiner* — Karlheinz R Skowronek
*Assistant Examiner* — Khalid Kader
(74) *Attorney, Agent, or Firm* — Quarles & Brady LLP

(57) ABSTRACT

The present disclosures provides isolated or purified compounds, each of which bind to a metal atom. Generally, the compounds are small in size (e.g., molecular weight of less than about 1 kDa) and peptidic in nature, inasmuch as the compounds comprise amino acids. In some embodiments, the compound comprises a structure of Formula I:

$$M_1\text{-}P_1\text{-}M_2\text{-}P_2$$

wherein each of $P_1$ and $P_2$ is a peptide comprising at least two amino acids, $M_1$ is a first metal binding moiety comprising a substituted imidazolone ring, $M_2$ is a second metal binding moiety comprising a substituted oxazolone ring, and wherein $M_1$ and $M_2$ bind to a single metal atom. Also provided are related complexes, conjugates, cells which synthesize the compounds of the present disclosures, substantially homogenous cultures thereof, kits and compositions, and methods of making or using the materials of the present disclosures.

34 Claims, 12 Drawing Sheets

(56) References Cited

PUBLICATIONS

Deydsh, et al. (1998) Acidophilic methanotrophic communities from sphagnum peat bogs. Appl Environ Microbiol 64: 922-929.

Dunfield, et al. (2003) *Methylocella silvestris* sp. nov., a novel methanotroph isolated from an acidic forest cambisol. Int J Syst Evol Microbiol 53: 1231-1239.

Dunfield, et al. (2007) Methane oxidation by an extremely acidophilic bacterium of the phylum Verrucomicrobia. Nature 450: 879-883.

Dunfield, et al. (2010) *Methylocapsa aurea* sp. nov., a facultatively methanotrophic bacterium possessing a particulate methane monooxygenase. Int J Syst Evol Microbiol doi: 10.1099/ ijs.0. 020149-0.

Fogel, et al. (1986) Biodegradation of chlorinated ethenes by a methane-utilizing mixed culture. Appl Environ Microbial 51: 720-724.

Han, et al. (2004) Quantification of gene expression in methanotrophs by competitive reverse transcription-polymerase chain reaction. Environ Microbiol 6: 388-399.

Hanson, et al. (1996) Methanotrophic bacteria. Microbiol Rev 60:439-471.

Hutchens, et al. (2004) Analysis of methanotrophic bacteria in Movile Cave by stable isotope probing. Environ Microbiol 6: 111-120.

Im, et al. (2010) Characterization of a novel facultative *Methylocystis* species capable of growth on methane, ethanol, and acetate. Submitted, Env Microbio Rep.

Islam, et al. (2008) Methane oxidation at 55 °C. and pH 2 by a thermoacidophilic bacterium belonging to the Verrucomicrobia phylum. Proc Natl Acad Sci 105: 300-304.

Jukes, et al. (1969) Evolution of protein molecules. New York: Academic Press.

Laemmli, et al. (1970) Cleavage of structural proteins during the assembly of the head of bacteriophage T4. Nature 227:680-685.

Leak, et al. (1986) Growth yields of methanotrophs. Appl Microbiol Biotechnol 23: 477-481.

Lee, et al. (2006) Mixed pollutant degradation by *Methylosinus trichosporium* OB3b expressing either soluble or particulate methane monooxygenase: can the tortoise beat the hare? Appl Environ Microbiol 72: 7503-7509.

Linton, et al. (1978) Growth of the methane utilizing bacterium *Methylococcus* NCIB 11083 in mineral salts medium with methanol as a sole source of carbon. FEMS Microbiol Lett 4, 125-128.

Maymo-Gatell, et al. (1999) Reductive dechlorination of chlorinated ethenes and 1,2-dichloroethane by "*Dehalococcoides ethenogenes*" 195. Appl Environ Microbiol 65: 3108-3113.

McDONALD, et al. (1995) Detection of methanotrophic bacteria in environmental samples with the PCR. App Environ Microbiol 61: 116-121.

Mesbah, et al. (1989) Precise measurement of the G+C content of deoxyribonucleic acid by high performance liquid chromatography. Int J Syst Bact 39: 159-167.

Morton, et al. (2000) Effect of copper speciation on whole-cell soluble methane monooxygenase activity in *Methylosinus trichosporium* OB3b. Appl Environ Microbiol 66: 1730-1733.

Murrell, et al. (2000) Regulation of expression of methane monooxygenases by copper ions. Trends Microbiol 8: 221-225.

Nielsen, et al. (1997) Copper-dependent reciprocal transcriptional regulation of methane monooxygenase genes in *Methylococcus capsulatus* and *Methylosinus trichosporium*. Mol Microbiol 25: 399-409.

Oldenhuis, et al. (1989) Degradation of chlorinated aliphatic hydrocarbons by *Methylosinus trichosporium* OB3b expressing soluble methane monooxygenase. Appl Environ Microbiol 55: 2819-2826.

Pol, et al. (2007) Methanotrophy below pH 1 by a new *Verrucomicrobia* species. Nature 450: 874-878.

Poret-Peterson, et al. (2008) Transcription of nitrification genes by the methane-oxidizing bacterium, *Methylococcus capsulatus* strain Bath. ISME J 2: 1213-1220.

Prior, et al. (1985) The effect of copper ions on membrane content and methane monooxygenase activity in methanol-grown cells of *Methylococcus capsulatus* (Bath). J Gen Microbiol 131: 155-163.

Rozen, et al. (2000) Primer3 on the WWW for general users and for biologist programmers. In Bioinformatics Methods and Protocols: Methods in Molecular Biology. Krawetz, S., Misener, S. (eds). Totowa, NJ, USA: Humana Press, pp. 365-386.

Saitou, et al. (1987) The neighbor-joining method: a new method for reconstructing phylogenetic trees. Mol Biol Evol 4: 406-425.

Scheutz, et al. (2004) Attenuation of methane and volatile organic compounds in landfill soil covers. J Environ Qual 33: 61-71.

Semprini, et al. (1990) A field evaluation of in-situ biodegradation of chlorinated ethenes: part 2, results of biostimulation and biotransformation experiments. Ground Wat 28:715-727.

Semrau, et al. (2010) Methanotrophs and copper. FEMS Microbiol Rev 34: 496-531.

Tamaoka, et al. (1984) Determination of DNA base composition by reversed-phase high-performance liquid chromatography. FEMS Microbiol Lett 25: 125-128.

Tamura, et al. (2007) MEGA4: molecular evolutionary genetics analysis (MEGA) software version 4.0. Mol Biol Evol 24: 1596-1599.

Tsien, et al. (1989) Biodegradation of trichloroethylene by *Methylosinus trichosporium* OB3b. Appl Environ Microbiol 55: 3155-3161.

Van Hylckama, et al. (1996) Transformation kinetics of chlorinated ethenes by *Methylosinus trichosporium* OB3b and detection of unstable epoxides by on-line gas chromatography. Appl Environ Microbiol 62: 3304-3312.

Van Hylckama, et al. (1997) Effect of chlorinated ethene conversion on viability and activity of *Methylosinus trichosporium* OB3b. Appl Environ Microbiol 63: 4961-4964.

Vela, et al. (1964) Improved stain for visualization of Azotobacter encystment. J Bacteriol 87: 476-477.

Wartiainen, et al. (2006) *Methylocystis rosea* sp. nov., a novel methanotrophic bacterium from Arctic wetland soil, Svalbard, Norway (78 ° N). Intl J Syst Evol Microbiol 56: 541-547.

Wayne et al. (1987) Report of the ad hoc committee on reconciliation of approaches to bacterial systematics. Intl J Syst Bacteriol 37: 463-464.

Whittenbury, et al. (1970) Enrichment, isolation and some properties of methane-utilizing bacteria. J Gen Microbiol 61:205-218.

Wilkinson, et al. (1974) Interactions in a mixed bacterial population growing on methane in continuous culture. Biotechnol Bioengin 16:41-59.

Yoon, et al. (2008) Measurement and modeling of multiple substrate oxidation by methanotrophs at 20° C. FEMS Microbiol Lett 287: 156-162.

Yoon, et al. (2010) An assay for screening microbial cultures for chalkophore production. Environ Microbiol Rep doi:10.1111/j. 1758-2229.2009.00125.x.

Zehr, et al. (1989) Use of degenerate oligonucleotides for amplification of the nifH gene from the marine cyanobacterium Trichodesmium thiebautii, Appl Environ Microbiol 55: 2522-2526.

Krentz, et al. (2010) A Comparison of *Methanobactins* from *Methylosinus trichosporium* OB3b and *Methylocystis* Strain SB2 Predicts *Methanobactins* Are Synthesized from Diverse Peptide Precursors Modified to Create a Common Core for Binding and Reducing Copper Ions, Biochemistry 10117-10130, DOI 10.1021/ bi1014375.

Im, et al. (2011) Pollutant degradation by a Methylocystis strain SB2 grown on ethanol: bioremediation via facultative methanotrophy, FEMS Microbiol Lett 318: 137-142.

\* cited by examiner

SEQUENCE LISTING

<160> NUMBER OF SEQ ID NOS: 6

<210> SEQ ID NO 1
<211> LENGTH: 1132
<212> TYPE: DNA

```
<213> ORGANISM: Artificial Sequence
<220> FEATURE:
<223> OTHER INFORMATION: Methylocystis sp. SB2 16S ribosomal RNA gene,
      partial sequence
<220> FEATURE:
<221> NAME/KEY: misc_feature
<222> LOCATION: (995)..(995)
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1084)..(1084)
<223> OTHER INFORMATION: n is a, c, g, or t
<220> FEATURE:
<221> NAME/KEY: misc_feature
<222> LOCATION: (1087)..(1087)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1106)..(1106)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t

<400> SEQUENCE: 1
gcgagcctac catgcaagtc gaacgcccta gcaataggga gtggcagacg ggtgagtaac       60
gcgtgggaac gtacccttcg gtctggaata acccagggaa acttgggcta ataccggata      120
cgtgcgagag cagaaagatt tatcgccgaa ggatcggccc gcgtccgatt agctagttgg      180
tgaggtaaaa gctcaccaag gcgacgatcg gtagctggtc tgagaggatg atcagccaca      240
ctgggactga gacacggccc agactcctac gggaggcagc agtggggaat attggacaat      300
gggcgaaagc ctgatccagc catgccgcgt gagtgatgaa ggccctaggg ttgtaaagct      360
ctttcgccag ggacgataat gacggtacct ggataagaag ccccggctaa cttcgtgcca      420
gcagccgcgg taatacgaag ggggctagcg ttgttcggat ttactgggcg taaagcgcac      480
gtaggcggat ttttaagtca ggggtgaaat cccaaggctc aaccttggaa ctgcctttga      540
tactggaagt ctcgagtccg ggagaggtga gtggaactgc gagtgtagag gtgaaattcg      600
tagatattcg caagaacacc agtggcgaag gcggctcact ggcccggtac tgacgctgag      660
gtgcgaaagc gtgggagca aacaggatta gataccctgg tagtccacgc cgtaaactat      720
ggatgctagc cgttgggcag cttgctgttc agtggcgcag ctaacgcttt aagcatcccg      780
cctggggagt acggtcgcaa gattaaaact caaaggaatt gacggggggcc cgcacaagcg      840 gtggagcatg tggtttaatt cgaagcaacg cgcagaacct taccagcttt tgacatgccc      900
ggtatgatcg ccagagatgg ctttcttccc cccaaggggc cggtgcacag gtgctgcatg      960
gctgtcgtca gctcgtgtcg tgagatgttg ggttnagtcc cgcaacgagc gcaaccctcn     1020
cccttagttg ccatcattaa nttggggcac tctaggggga ctgccggtga taaccccccc     1080
aagnaangtg ggggaatnac ctcaantccn catggccctt acaggctggg ct             1132

<210> SEQ ID NO 2
<211> LENGTH: 447
```

```
<212> TYPE: DNA
<213> ORGANISM: Artificial Sequence
<220> FEATURE:
<223> OTHER INFORMATION: Methylocystis sp. SB2 particulate methane
      monooxygenase (pmoA) gene, partial cds

<400> SEQUENCE: 2
cgacggtcgt gccgattctc ggcgtgacct tctgcgccgc ggcgcaggcg ttctggtggg      60
tgaacttccg tctgccgttc ggcgcggtgt tcgcggctct tggcctgctg attggcgagt     120
ggatcaaccg ctacgtcaac ttctggggct ggacctactt cccgatcagc cttgtgttcc     180
cgtccgctct gatcgttccg gcgatctggc ttgacgtgat cctgcttctg tcgggctcct     240
atgtgatcac ggcgattgtt ggttcgctcg gctggggtct gttgttctac ccgaacaact     300
ggccggcgat tgcggcgttc caccaggcga cggagcagca tggtcagctg atgacgcttg     360
cggatctgat cggcttccac ttcgtccgca cctcgatgcc ggaatatatc cgcatggtcg     420
agcgcggcac gctgcgcacc ttcggta                                         447

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
agtggaactg cgagtgtaga ggtg                                             24

<210> SEQ ID NO 4
<211> LENGTH: 25
<212> TYPE: DNA
<213> ORGANISM: Artificial Sequence
<220> FEATURE:
<223> OTHER INFORMATION: primer

<400> SEQUENCE: 4
accagggtat ctaatcctgt ttgct                                            25

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
ggatcaaccg ctacgtcaac ttct                                             24

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
agccgagcga accaacaatc                                                  20
```

METHYLOCYSTIS STRAIN SB2 MATERIALS AND METHODS

CROSS-REFERENCE TO RELATED APPLICATIONS

This application claims priority from U.S. provisional patent application Ser. No. 61/371,447 filed Aug. 6, 2010. This application is incorporated herein by reference in its entirety.

STATEMENT REGARDING FEDERALLY SPONSORED RESEARCH OR DEVELOPMENT

This invention was made with government support under DE-FC2 6-05NT42431 awarded by the Department of Energy. The U.S. government has certain rights in the invention.

BACKGROUND

Bioremediation is a process in which microorganisms, fungi, green plants, or their enzymes are used to restore the natural environment, altered by contaminants, to its original condition. Bioremediation may be employed, for example, to attack specific soil contaminants, such as degradation of chlorinated hydrocarbons, by bacteria or to cleanup oil spills by the addition of nitrate and/or sulfate fertilisers to facilitate the decomposition of crude oil by exogenous bacteria. Additional examples of bioremediation technologies include bioventing, landfarming, bioreactor, composting, bioaugmentation, rhizofiltration, and biostimulation.

Bioremediation technologies may be generally classified as in situ or ex situ. In situ bioremediation involves treating the contaminated material at the site, while ex situ bioremediation involves the removal of the contaminated material to be treated elsewhere.

There are a number of cost/efficiency advantages to bioremediation. For example, introducing a microorganism into an environment to reduce the concentration of a contaminant in situ, is typically much less expensive than excavating followed by disposal off site, incineration, or other ex situ technologies.

However, not all contaminants are easily treated by bioremediation using microorganisms. For example, heavy metals (including, for example, cadmium and lead) are not readily absorbed or captured by organisms. The heavy metals in harvested biomass may be further concentrated by incineration or even recycled for industrial use. Motivations for controlling heavy metal concentrations in gas streams are diverse. Some of them are dangerous to health or to the environment (e.g., Hg, Cd, As, Pb, Cr), some may cause corrosion (e.g., Zn, Pb), while some are harmful in other ways (e.g., arsenic may pollute catalysts). Within the European community the elements of high concern are As, Cd, Co, Cr, Cu, Hg, Mn, Ni, Pb, Sn, and Tl, the emissions of which are regulated in waste incinerators. Some of these elements are actually necessary for humans in minute amounts (Co, Cu, Cr, Mn, Ni), while others are carcinogenic or toxic, affecting, among others, the central nervous system (Mn, Hg, Pb, As), the kidneys or liver (Hg, Pb, Cd, Cu) or skin, bones, or teeth (Ni, Cd, Cu, Cr) (Zevenhoven et al., *Control of Pollutants in Flue Gases and Fuel Gases*. TKK, Espoo (2001)).

Heavy metal pollution most commonly arises from the purification of metals, e.g., the smelting of copper and the preparation of nuclear fuels. Electroplating is the primary source of chromium and cadmium. Through precipitation of their compounds or by ion exchange into soils and muds, heavy metal pollutants can localize and lay dormant. Unlike organic pollutants, heavy metals do not decay and thus pose a different kind of challenge for remediation.

Once in the atmosphere, mercury is widely disseminated and can circulate for years, accounting for its wide-spread distribution. Alkali and metal processing, incineration of coal, and medical and other waste, and mining of gold and mercury contribute greatly to mercury concentrations in some areas, but atmospheric deposition is the dominant source of mercury over most of the landscape. Natural sources of atmospheric mercury include volcanoes, geologic deposits of mercury, and volatilization from the ocean. In areas where mercury has accumulated through industrial or mining activities, natural processes may bury, dilute, or erode the mercury deposits, resulting in declines in concentration. In many areas, however, mercury concentrations have actually increased because atmospheric deposition has increased. Concentrations of mercury in feathers of fish-eating seabirds from the northeastern Atlantic Ocean, for example, have steadily increased for more than a century. In certain North American sediment cores, sediments deposited have mercury concentrations about 3-5 times those found in older sediments. Some sites are considered methylmercury "hot spots" due to inadvertent human activities. Lake acidification, addition of substances like sulfur that stimulate methylation, and mobilization of mercury in soils in newly flooded reservoirs or constructed wetlands have been shown to increase the likelihood that mercury will become a problem in fish. Therefore, it would be advantageous to develop novel compositions and methods for efficiently binding at least one metal atom.

BRIEF SUMMARY OF THE INVENTION

The present disclosures provide isolated or purified compounds that bind to a metal atom. Generally, the compounds are small in size (having a molecular weight of less than, e.g., 1 kDa) and peptidic in nature, inasmuch as the compounds comprise amino acids connected via a peptide bond.

In some embodiments, the compound comprises at least four amino acids, a first metal binding moiety comprising a substituted imidazolone ring ($M_1$), and a second metal binding moiety comprising a substituted oxazolone ring ($M_2$), wherein $M_1$ and $M_2$ bind to a single metal atom.

In some embodiments, the compound comprises a structure of Formula I:

$$M_1\text{-}P_1\text{-}M_2\text{-}P_2 \qquad \text{[Formula I]}$$

wherein each of $P_1$ and $P_2$ is a peptide comprising at least two amino acids, $M_1$ is a first metal binding moiety comprising a substituted imidazolone ring, $M_2$ is a second metal binding moiety comprising a substituted oxazolone ring, and wherein $M_1$ and $M_2$ bind to a single metal atom.

Also provided are complexes comprising a compound of the present disclosures and a metal atom, wherein the compound is bound to the metal atom. Conjugates comprising a compound or complex of the present disclosures and a heterologous moiety (or conjugate moiety) are further provided herein.

The present disclosures furthermore provide cells which synthesize the compounds or complexes of the present disclosures, as well as cultures (e.g., substantially homogenous cultures) comprising such cells. Related kits and compositions, each of which comprise a compound, complex, conjugate, cell, or culture, of the present disclosures are moreover provided herein.

The present disclosures further provide methods of making the compounds described herein, and uses of the compounds, cells, cultures (and other related materials described herein) for bioremediation.

The present disclosures also provide methods for binding and reducing the redox state of metals in a system.

The present disclosures also provide methods for reducing the concentration chlorinated compounds, methane, ethanol, and/or acetate from a system.

The present disclosures further provide methods for producing a nanoparticle comprising a metal atom.

The present disclosures further provide methods for oxidizing water from a system.

DETAILED DESCRIPTION OF THE INVENTION

Metal Binding Compounds

Figure 1:
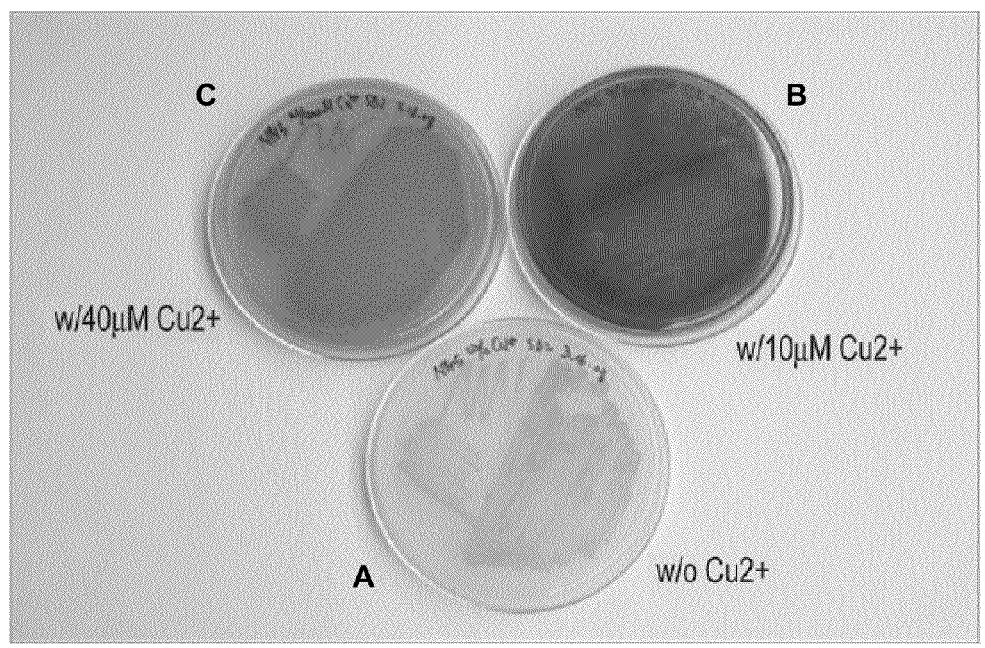
FIG. 1 represents the coloration of *Methylocystis* strain SB2 after 4 weeks of incubation on NMS medium with either (A) no added copper; (B) 10 µM Cu added as $CuCl_2$, or; (C) 40 µM Cu added as $CuCl_2$. 80×53 mm (600×600 DPI).

The present disclosures provide a compound that binds to a metal atom and which may be used, for example, in the bioremediation of metal-contaminated systems. In some embodiments, the compound binds to a transition metal, e.g., an element whose atom has an incomplete "d" sub-shell, or which can give rise to cations with an incomplete "d" sub-shell or any element in the d-block of the periodic table. In some aspects, the transition metal is copper, cadmium, cobalt, chromium, mercury, gold, iron, nickel, zinc, silver, lead, aluminum, manganese, uranium, or a combination thereof. In some embodiments, the compound binds to all or a combination of copper, cadmium, cobalt, chromium, mercury, gold, iron, nickel, and zinc. In some aspects, the compound binds preferentially to one or a subset of these metals. In specific embodiments, the compound preferentially binds to copper, inasmuch as the dissociation constant (Kd) for copper is greater than the Kd for any other metal atom. In some embodiments, the compound of the present disclosures binds to any oxidation state of the transition metal. In some aspects, the compound binds to one or more of: Au(III), Cd(II), Co(II), Cr(VI), Cu(I), Cu(II), Fe(II), Fe(III), Hg(I), Hg(II), Ni(II), Zn(II), Ag(I), Pb(II), Pb(IV), Al(III), Mn(II), Mn(III), Mn(IV), Mn(VI), Mn(VII), U(IV), and/or U(VI).

In some embodiments of the present disclosures, the compound binds to a metal atom through one or two metal binding moieties: $M_1$ and $M_2$. In some aspects, the compound is a bidentate ligand that chelates the metal atom, e.g., the central metal atom. As used herein, the term "bidentate ligand" refers to a chelating agent having two groups capable of attachment to a metal ion. Also, as used herein, the term "chelation" refers to the formation of two or more separate bindings between a bi- or poly-dentate ligand and a single central atom. In some aspects, the two groups of the compound that attach to a metal ion are $M_1$ and $M_2$. Accordingly, in some embodiments, the compound comprises a first metal binding moiety $M_1$, and a second metal binding moiety, $M_2$, wherein $M_1$ and $M_2$ bind a metal atom, e.g., chelate the metal atom.

In some embodiments, the compound comprises a first metal binding moiety $M_1$ comprising a substituted imidazolone ring, and a second metal binding moiety $M_2$ comprising a substituted oxazolone ring, wherein $M_1$ and $M_2$ bind to a single metal atom.

In some aspects, $M_1$ comprises a structure of Formula IIa:

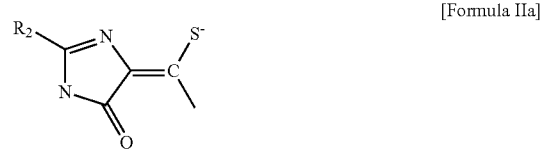

[Formula IIa]

wherein $R_2$ comprises a side chain of an amino acid.

In some aspects, $M_2$ comprises a structure of Formula IIb:

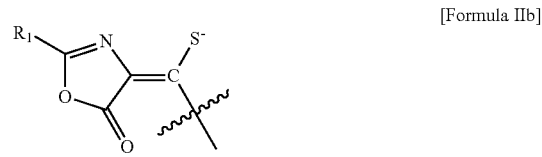

[Formula IIb]

wherein $R_1$ comprises a side chain of an amino acid.

With regard to $R_2$ of Formula IIa and $R_1$ of Formula IIb, the side chain is, in various aspects, derived from the side chain and backbone atoms of a naturally-occurring amino acid or a non-coded amino acid. As used herein, the term "naturally-occurring amino acid" is synonymous with the term "coded amino acid" which as used herein refers to an amino acid that is an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr. "Non-coded" as used herein refers to an amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr. In some embodiments, $R_1$ comprises a side chain along with the backbone nitrogen and alpha-carbon atoms of a naturally-occurring amino acid, or in the alternative $R_1$ comprises a side chain along with the backbone nitrogen and alpha-carbon atoms of a non-coded amino acid. In some embodiments, $R_2$ comprises a side chain along with the alpha-carbon of a naturally-occurring amino acid, which is oxidized to an oxo group, or in the alternative $R_2$ comprises a side chain with the alpha-carbon of a non-coded amino acid, which is oxidized to an oxo group. A compound is provided wherein $R_1$ comprises a side chain along with the backbone nitrogen and alpha-carbon atoms of a naturally-occurring amino acid or a non-coded amino acid. A compound is also provided wherein $R_1$ comprises a side chain along with the backbone nitrogen and alpha-carbon atoms of a naturally-occurring amino acid and $R_2$ comprises a side chain with the alpha-carbon of a non-coded amino acid, which is oxidized to an oxo group, or wherein $R_2$ comprises a side chain with the alpha-carbon of a naturally-occurring amino acid, which is oxidized to an oxo group, and $R_1$ comprises a side chain along with the backbone nitrogen and alpha-carbon atoms of a non-coded amino acid.

The disclosures further contemplate a compound wherein $R_1$ of Formula IIb comprises a structure of Formula III, wherein Formula III is attached as $R_1$ to the structure of Formula IIb at the indicated attachment point;

[Formula III]

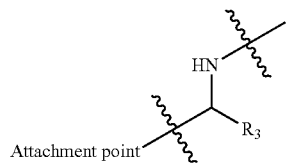

and wherein $R_3$ is a hydroxyalkyl or an alkylated sulfate.

In some embodiments, the hydroxyalkyl comprises Structure I:

wherein m is an integer between 1 and 6. Also provided are compounds wherein the hydroxyalkyl comprises C1-C4 alkyl, e.g., C1, C2, a branched or linear C3 or C4 alkyl. In some aspects, the hydroxyalkyl comprises —$CH(CH_3)OH$.

In some embodiments, the alkylated sulfate comprises Structure II:

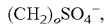

wherein o is an integer between 1 and 6. Compounds contemplated include those wherein the alkylated sulfate comprises C1-C4 alkyl, e.g., C1, C2, a branched or linear C3 or C4 alkyl. In particular aspects, the alkylated sulfate is —$CH(CH_3)SO_4^-$.

Compounds are also provided wherein $R_2$ of Formula IIa comprises an alkylated guanidinium moiety. In some aspects, $R_2$ of Formula IIa comprises a structure of Formula IV:

[Formula IV]

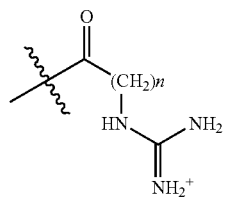

wherein n is an integer between 1 and 5. In certain aspects, n is 1, 2, 3, 4, or 5. In specific aspects n is 3.

In exemplary embodiments of the present disclosures, $M_2$ comprises a structure of Formula IIb, wherein $R_1$ comprises a structure of Formula III, and $M_1$ comprises a structure of Formula IIa, wherein $R_2$ comprises a structure of Formula IV.

Amino Acids

The compounds of the present disclosures are generally peptidic in nature, inasmuch as the compounds comprise amino acids, e.g., two or more amino acids, connected via one or more peptide bonds. The amino acids of the compounds of the present disclosures may be naturally-occurring amino acids or may be non-coded amino acids, including, but not limited to, any of those previously described herein. The compound, in some embodiments, comprise two, three, four, or five amino acids. In exemplary embodiments, the compound comprises four amino acids, a first metal binding moiety comprising a substituted imidazolone ring ($M_1$), and a second metal binding moiety comprising a substituted oxazolone ring ($M_2$), wherein $M_1$ and $M_2$ bind to a single metal atom.

In certain aspects, the compound comprises a structure of Formula I:

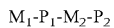 [Formula I]

wherein each of $P_1$ and $P_2$ is a peptide comprising at least two amino acids, $M_1$ is a first metal binding moiety comprising a substituted imidazolone ring, $M_2$ is a second metal binding moiety comprising a substituted oxazolone ring, and wherein $M_1$ and $M_2$ bind to a single metal atom.

In some aspects, $P_1$ is a dipeptide. In some aspects, $P_2$ is a dipeptide or tripeptide. In some aspects, each of $P_1$ and $P_2$ is a dipeptide.

Compounds provided include those wherein $P_2$ comprises a structure of $aa_3$-$aa_4$, or wherein $P_2$ comprises a structure of $aa_3$-$aa_4$-$aa_5$, wherein each of $aa_3$, $aa_4$ and $aa_5$ is a small aliphatic amino acid. In certain aspects, $P_1$ comprises a structure of $aa_1$-$aa_2$, wherein $aa_2$ is a sulfur-containing amino acid or a hydroxyl-containing amino acid and $aa_1$ is a small aliphatic amino acid. In some aspects, each of $aa_1$, $aa_3$, $aa_4$ and $aa_5$ is a small amino acid independently selected from the group consisting of: Ala, Gly, Ser, Thr, Pro, or a conservative amino acid substitution thereof. In some aspects, $aa_2$ is Ser, cysteic acid or a conservative amino acid substitution thereof. As used herein, the term "conservative amino acid substitution" is the replacement of one amino acid with another amino acid having similar properties, e.g., size, charge, hydrophobicity, hydrophilicity, and/or aromaticity, and includes exchanges within one of the following five groups:

I. Small aliphatic, nonpolar or slightly polar residues:

Ala, Ser, Thr, Pro, Gly;

II. Polar, negative-charged residues and their amides and esters:

Asp, Asn, Glu, Gln, cysteic acid and homocysteic acid;

III. Polar, positive-charged residues:

His, Arg, Lys; Ornithine (Orn)

IV. Large, aliphatic, nonpolar residues:

Met, Leu, Ile, Val, Cys, Norleucine (Nle), homocysteine

V. Large, aromatic residues:

Phe, Tyr, Trp, acetyl phenylalanine

Compounds are also provided wherein one or more of the amino acids of the compound of the present disclosures is additionally modified. For example, in some embodiments, one or more of the amino acids may be glycosylated, amidated, carboxylated, phosphorylated, esterified, N-acylated, cyclized via, e.g., a disulfide bridge, or converted into an acid addition salt and/or optionally dimerized or polymerized, or conjugated.

In one embodiment, the compound, when bound to a single metal atom, comprises the structure of:

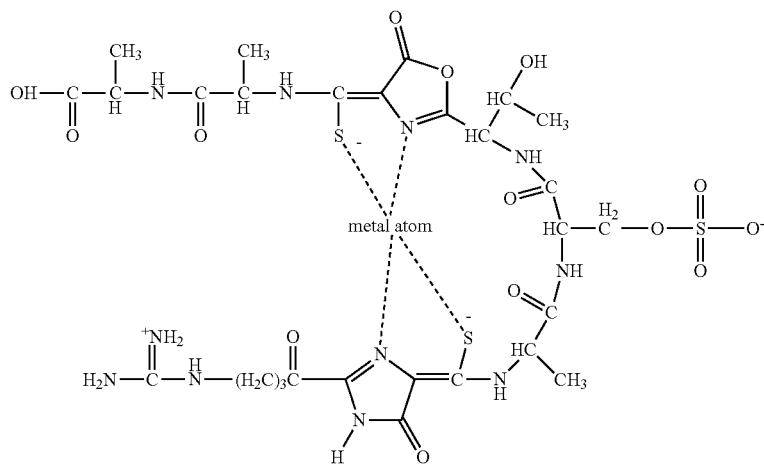

In an alternative embodiment, the compound, when bound to a single metal atom, comprises the structure of:

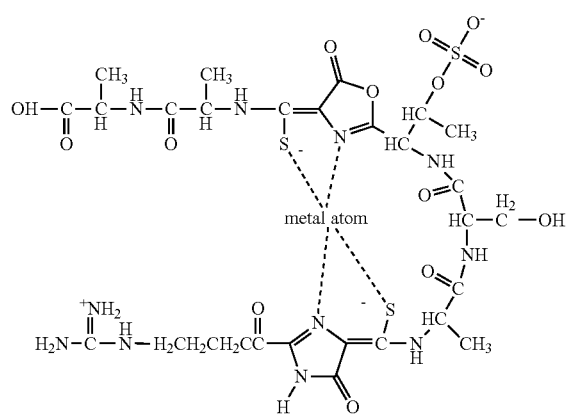

Size

The compound of the present disclosures is generally small in size. In some aspects, the compound has a molecular weight which is less than or about 1.05 kDa (1050 Daltons). Alternatively, the compound has a molecular weight which is less than or about 1.04 kDa, less than or about 1.03 kDa, less than or about 1.02 kDa, less than or about 1.01 kDa, less than or about 1.00 kDa, less than or about 0.99 kDa, less than or about 0.98 kDa, less than or about 0.97 kDa, less than or about 0.96 kDa, less than or about 0.95 kDa, less than or about 0.94 kDa, less than or about 0.93 kDa, or less than or about 0.92 kDa.

The compound contemplated by the present disclosures has, in various aspects, a molecular weight which is at least or about 0.80 kDa, at least or about 0.81 kDa, at least or about 0.82 kDa, at least or about 0.83 kDa, at least or about 0.84 kDa, at least or about 0.85 kDa, at least or about 0.86 kDa, at least or about 0.87 kDa, at least or about 0.88 kDa, at least or about 0.89 kDa, at least or about 0.90 kDa, at least or about 0.91 kDa.

In one preferred embodiment, the compound is bound to $Cu^+$ and has a mass of about 0.9131 kDa. In another preferred embodiment, the compound is in the neutral, unbound form, and has a mass of about 0.81520 kDa.

Isolated, Purified

In some embodiments, the compound of the present disclosures is isolated and/or purified. The term "isolated" as used herein means having been removed from its natural environment. The term "purified" as used herein means having been increased in purity, wherein "purity" is a relative term, and not to be necessarily construed as absolute purity. For example, the purity in various aspects is at least about 50%, at least or about 60%, at least or about 65%, at least or about 70%, at least or about 75%, at least or about 80%, at least or about 85%, at least or about 90%, at least or about 93%, at least or about 95%, at least or about 96%, at least or about 97%, at least or about 98%, at least or about 99%, or about 100%. Methods of isolating and/or purifying the compounds of the present disclosures are further described herein.

Methods of Making

The compounds of the present disclosures include at least one made by and isolated from cells. In some embodiments, the cells are bacterial cells which naturally produce the compound (e.g., cells which naturally comprise the enzymes and cellular machinery necessary to produce the compound). In certain aspects, the cells are facultative methanotrophs, which, for example, utilize methane, ethanol, or acetate for growth. In specific aspects, the methanotrophic cells express a particulate methane monooxygenase (pMMO) in the presence of either methane or ethanol. For example, in some aspects, the cells express a particulate methane monooxygenase (pMMO) in the absence of methane and in the presence of acetate or ethanol; in some aspects, the cells express a particulate methane monooxygenase (pMMO) in the absence of ethanol and in the presence of methane or acetate. In some aspects, the cells do not express a soluble or cytoplasmic form of methane monooxygenase (sMMO) but do express a pMMO. In some aspects of the present disclosures, the cells are bacterial cells of the genus *Methylocystis*. In some specific aspects, the cells are cells of a *Methylocystis* strain SB2, which was deposited with the American Type Culture Collection (ATCC; Manassas, Va.) as ATCC Patent Deposit Designation No. PTA-10927, on May 6, 2010. Progeny of a cell line derived from a cell of *Methylocystis* strain SB2, deposited as ATCC, Patent Deposit Designation No. PTA-10927, on May 6, 2010, are also contemplated as aspects of the disclosures.

Also provided are host cells which have been modified, e.g., genetically modified, to contain the enzymes and cellular machinery necessary to produce the compound. In some embodiments, the host cells which produce the compound are recombinant cells comprising one or more recombinant expression vectors, each comprising a nucleic acid molecule encoding the gene(s) involved in the synthesis of the compound.

Accordingly, the present disclosures provide a method of making any of the metal-binding compounds described herein. In some embodiments, the method comprises culturing a cell which naturally produces the compound (e.g., cells which naturally comprise the enzymes and cellular machinery necessary to produce the compound) under conditions necessary to produce the compound and isolating the compound from the cells. In specific aspects, the cells are any of the cells described herein that naturally produce enzymes and cellular machinery necessary to produce the compound. As an example, the cells that naturally produce enzymes and cellular machinery necessary to produce the compound are of the *Methylocystis* strain SB2. A method is also provided which comprises culturing cells which have been modified, e.g., genetically modified, to contain the enzymes and cellular machinery necessary to produce the compound, under conditions necessary to produce the compound and isolating the compound from the cells. Modified cells include host cells comprising a nucleic acid molecule encoding a nonribosomal peptide synthetase involved in the synthesis of the compound.

In some aspects, the cells are bacterial cells which naturally produce the compound (e.g., cells which naturally comprise the enzymes and cellular machinery necessary to produce the compound) and the cells are cultured in accordance with the descriptions found herein. For example, the cells in some aspects are cultured at a pH between 6 and 9, inclusive, necessarily including pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6, pH 8.7, pH 8.8, pH 8.9, and pH 9.0. In some aspects, the cells are cultured at a temperature below 37° C., below 36° C., below 35° C., below 34° C., below 33° C., below 32° C., below 31° C., or below 30° C. In some aspects, the cells are cultured at a temperature above 5° C., above 6° C., above 7° C., above 8° C., or above 9° C. In some aspects, the cells are cultured at a temperature between about 10° C. and 30° C.

In alternative embodiments, the compounds of the present disclosures are synthesized using known chemistry techniques, without the use of cells. For example, a desired polypeptide backbone is prepared using solid phase peptide synthesis, as previously described in Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwood et al., Oxford University Press, Oxford, United Kingdom, 2000; and U.S. Pat. No. 5,449,752. Each oxazole ring can be formed by cyclizing an internal amino acid having a hydroxyl moiety on its side chain with the alpha-carboxyl group of an adjacent amino acid. Subsequent dehydration results in the imine of the oxazole ring. Other modifications of the oxazole ring (e.g., oxidation) can be performed using known methods as described in, for example, March et al., Advanced Organic Chemistry, 6th ed., John Wiley & Sons, Hoboken, N.J., 2007.

The compounds of the present disclosures are optionally isolated or purified using standard techniques known in the art. For example, the compounds are, in various aspects, purified upon chemical synthesis via HPLC, crystallization, affinity chromatography, or through the use of magnetic beads or metal-based or metal-coated beads. In exemplary embodiments, the compound may be isolated from cells through filtration, centrifugation, affinity chromatography, or through the use of magnetic beads or metal-based or metal-coated beads.

Cells

The present disclosures further provides cells which synthesize the compounds as described herein, e.g., a compound having a molecular weight of less than 1 kDa and comprising at least four amino acids, a first metal binding moiety comprising a substituted imidazolone ring ($M_1$), and a second metal binding moiety comprising a substituted oxazolone ring ($M_2$), wherein $M_1$ and $M_2$ bind to a single metal atom. The cells in some aspects produce a compound comprising a structure of Formula I, as described herein. In some embodiments, the cells are isolated or purified.

In some embodiments, the cells are bacterial cells which naturally produce the compound (e.g., cells which naturally comprise the enzymes and cellular machinery necessary to produce the compound). In certain aspects, the cells are facultative methanotrophs, which, for example, utilize methane, ethanol, or acetate for growth. In specific aspects, the methanotrophic cells express a particulate methane monooxygenase (pMMO) in the presence of either methane or ethanol. For example, in some aspects, the cells express a pMMO in the absence of methane and in the presence of acetate or ethanol; in some aspects, the cells express a pMMO in the absence of ethanol and in the presence of methane or acetate. In some aspects, the cells express a pMMO in the presence of methane, acetate, or ethanol, but do not express a soluble or cytoplasmic form of a methane monooxygenase (sMMO). In some aspects of the present disclosures, the cells are bacterial cells of the genus *Methylocystis*. In some aspects, the cells are not cells of the strain H2s described in Belova et al., *Environ Microbiol Reports*, e-publication, 2010. In some specific aspects, the cells are cells of *Methylocystis* strain SB2, which was deposited with the American Type Culture Collection (ATCC; Manassas, Va.) as ATCC Patent Deposit Designation No. PTA-10927, on May 6, 2010. In some embodiments, the cells are progeny of a cell line derived from a cell of *Methylocystis* strain SB2, deposited as ATCC Patent Deposit Designation No. PTA-10927, on May 6, 2010.

In some embodiments, the cells are host cells which have been modified, e.g., genetically modified, to contain the enzymes and cellular machinery necessary to produce the compound. In some embodiments, the host cells which produce the compound are recombinant cells. In some aspects, the host cells comprise one or more recombinant expression vectors, each comprising a nucleic acid molecule encoding gene(s) involved in the synthesis of the compound. In some aspects, the host cells are bacterial cells but are not of the genus *Methylocystis*. In exemplary embodiments, the host cells are *E. coli* cells.

The cells of the present disclosures may be provided as a cell culture. Accordingly, in some embodiments, the present disclosures provides a substantially homogeneous culture comprising any of the cells described herein which produce a compound of the present disclosures. By "substantially homogenous" as used herein is meant that the culture is essentially free of all other types of cells which do not produce the compound. In some aspects, less than or about 25% (e.g., less than or about 20%, less than or about 15%, less than or about 10%, less than or about 5%, less than or about 3%, less than or about 1%) of the total cell population of the culture are cells which do not produce the compound. In some aspects, the culture is at least or about 75% homogenous, at least or about 80% homogenous, at least or about 85% homogenous, at least or about 90% homogenous, at least or about 95% homogenous for the cells which produce the compound. In some aspects, the culture is a clonal population of cells in which all cells of the culture are genetically identical.

In some embodiments, the culture is a liquid culture, e.g., the culture is maintained in a liquid medium. In some embodiments, the culture is a solid culture, e.g., the culture is maintained on a solid medium. The culture in some embodiments comprise nutrients essential to the growth of the cell, e.g., nitrogen source, e.g., dinitrogen, nitrate, ammonium, L-isoleucine, L-proline, L-glutamine), carbon source, e.g., methane, ethanol, acetate. In some embodiments, the cells, e.g., SB2 cells, are cultured in medium comprising methane, acetate, ethanol, or a combination of two or all of the foregoing. In some embodiments, the cells, e.g., SB2 cells are cultured in medium comprising copper (e.g., medium comprising $CuCl_2$). In alternative embodiments, the cells, e.g., SB2 cells are cultured in medium lacking copper (e.g., medium lacking $CuCl_2$). In some embodiments, the cells, e.g., SB2 cells, are cultured in medium comprising nitrate (e.g., nitrate mineral salt).

Complexes

The present disclosures further provide an isolated or purified complex comprising a compound of the present disclosures and a metal atom, wherein the compound is bound (e.g., chelated) to the metal atom. In some aspects, the compound is bound (e.g., chelated) to the metal atom via $M_1$ and $M_2$. In some aspects, the complex comprises the compound chelated to a transition metal, such as any of those described herein. In some aspects, the transition metal is selected from the group consisting of: copper, cadmium, cobalt, chromium, iron, nickel, zinc, silver, lead, aluminum, manganese, uranium or a combination thereof. In some aspects, the complex comprises the compound of the present disclosures bound, e.g., chelated, to Au(III), Cd(II), Co(II), Cr(VI), Cu(I), Cu(II), Fe(II), Fe(III), Hg(I), Hg(II), Ni(II), Zn(II), Ag(I), Pb(II), Pb(IV), Al(III), Mn(II), Mn(III), Mn(IV), Mn(VI), Mn(VII), U(IV), U(VI), or a combination thereof. In some aspects, the complex comprises a compound of the present disclosures and a copper atom.

Conjugates

The present disclosures further provides conjugates comprising a metal-binding compound as described herein, optionally in bound, e.g., chelated, form to a metal atom, and a heterologous moiety. As used herein, the term "heterologous moiety" is synonymous with the term "conjugate moiety" and refers to any molecule (chemical or biochemical, naturally-occurring or non-coded) which is different from the compounds described herein. Exemplary conjugate moieties that are contemplated include but are not limited to a heterologous peptide or polypeptide (e.g., a peptide of polypeptide that is distinct from a peptide of the compound), a targeting agent, an immunoglobulin or portion thereof (e.g., variable region, CDR, or Fc region), a diagnostic label such as a radioisotope, fluorophore or enzymatic label, a polymer including water soluble polymers, or other therapeutic or diagnostic agents. The conjugate in some embodiments comprises one or more of the metal-binding compounds of the present disclosures and one or more of: a peptide, a polypeptide, a nucleic acid molecule, a lipid, a carbohydrate, an antibody or fragment thereof, a polymer, a quantum dot, a small molecule, a toxin, a diagnostic agent, a carbohydrate, an amino acid.

In some embodiments, the heterologous moiety is a polymer. In some embodiments, the polymer is selected from the group consisting of: polyamides, polycarbonates, polyalkylenes and derivatives thereof including, polyalkylene glycols, polyalkylene oxides, polyalkylene terepthalates, polymers of acrylic and methacrylic esters, including poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

In some aspects, the polymer is a biodegradable polymer, including a synthetic biodegradable polymer (e.g., polymers of lactic acid and glycolic acid, polyanhydrides, poly(ortho) esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

In some aspects, the polymer is a bioadhesive polymer, such as a bioerodible hydrogel described by H. S. Sawhney, C. P. Pathak and J. A. Hubbell in *Macromolecules,* 1993, 26, 581-587, which is hereby incorporated by reference in its entirety, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In some embodiments, the polymer is a water-soluble polymer or a hydrophilic polymer. Hydrophilic polymers are further described herein under "Hydrophilic Moieties." Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof.

In specific embodiments, the polymer is a polyalkylene glycol, including, for example, polyethylene glycol (PEG).

In some embodiments, the heterologous moiety is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

In some embodiments, the heterologous moiety is a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid.

In some embodiments, the heterologous moiety is attached via non-covalent or covalent bonding to the compound of the present disclosures. In certain aspects, the heterologous moiety is attached to the compound of the present disclosures via a linker. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other.

The compound in some embodiments is linked to a conjugate moiety via direct covalent linkage by reacting targeted amino acid residues of the compound with an organic derivatizing agent that is capable of reacting with selected side chains or the N- or C-terminal residues of these targeted amino acids. Reactive groups on the compound or conjugate moiety include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, the conjugate moieties can be linked to the compound indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

Cysteinyl residues are most commonly reacted with α-haloacetates (and corresponding amines), such as chloroacetic acid, chloroacetamide to give carboxymethyl or carboxyamidomethyl derivatives. Cysteinyl residues also are derivatized by reaction with bromotrifluoroacetone, alpha-bromo-β-(5-imidozoyl)propionic acid, chloroacetyl phosphate, N-alkyl-maleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction may be performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Other modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)), deamidation of asparagine or glutamine, acetylation of the N-terminal amine, and/or amidation or esterification of the C-terminal carboxylic acid group.

Another type of covalent modification involves chemically or enzymatically coupling glycosides to the compound. Sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of tyrosine, or tryptophan, or (f) the amide group of glutamine. These methods are described in WO87/05330 published 11 Sep. 1987, and in Aplin and Wriston, *CRC Crit. Rev. Biochem.*, pp. 259-306 (1981).

In some embodiments, the compound is conjugated to a heterologous moiety via covalent linkage between a side chain of an amino acid of the compound and the heterologous moiety. In some embodiments, the conjugate comprises a linker that joins the compound to the heterologous moiety. In some aspects, the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, the length of the linker is long enough to reduce the potential for steric hindrance. If the linker is a covalent bond or a peptidyl bond and the conjugate is a polypeptide, the entire conjugate can be a fusion peptide. Such peptidyl linkers may be any length. Exemplary linkers are from about 1 to 50 amino acids in length, 5 to 50, 3 to 5, 5 to 10, 5 to 15, or 10 to 30 amino acids in length. Such fusion proteins may alternatively be produced by recombinant genetic engineering methods known to one of ordinary skill in the art.

The present disclosures further provide multimers or dimers of the compounds disclosed herein, including homo- or hetero-multimers or homo- or hetero-dimers. Two or more of the compounds can be linked together using standard linking agents and procedures known to those skilled in the art. For example, dimers can be formed between two compounds through the use of bifunctional thiol crosslinkers and bi-functional amine crosslinkers. The dimer can be a homodimer or alternatively can be a heterodimer. In certain embodiments, the linker connecting the two (or more) analogs is PEG. In some embodiments, the linker is a disulfide bond. For example, each monomer of the dimer may comprise a Cys residue (e.g., a terminal or internally positioned Cys) and the sulfur atom of each Cys residue participates in the formation of the disulfide bond. In some aspects, the monomers are connected via terminal amino acids (e.g., N-terminal or C-terminal), via internal amino acids, or via a terminal amino acid of at least one monomer and an internal amino acid of at least one other monomer. In specific aspects, the monomers are not connected via an N-terminal amino acid. In some aspects, the monomers of the multimer are attached together in a "tail-to-tail" orientation in which the C-terminal amino acids of each monomer are attached together or a "head-to-head" orientation in which the N-terminal amino acids of each monomer are attached together.

Compositions

The present disclosures further provide a composition comprising a biomass made with the cell or culture of the present disclosures. In some embodiments, the composition comprises a biomass produced by lysing the cells or culture of the present disclosures with, for example, a detergent, or lysing the cells via centrifugation. In some aspects, the composition comprises a biomass resulting from centrifuging the cells or culture of the present disclosures, optionally after lysing the cells with, e.g., a detergent. In some aspects, the biomass is the resulting supernatant obtained upon centrifuging the cells or culture of the present disclosures. In some aspects, the biomass is the resulting pellet obtained upon centrifuging the cells or culture of the present disclosures.

In some embodiments, the composition is sterile. In some aspects, the composition comprises a purified fraction of lysed and/or centrifuged cells or culture of the present disclosures.

Kits

The present disclosures further provides a kit comprising a compound, a complex, a conjugate, a cell, a culture, a composition, or a combination thereof, and instructions for use. In some embodiments in which the kit comprises cells or a culture, the cells or culture is cryopreserved. In some aspects, in which the kit comprises cells or a culture, the kit further comprises a medium comprising one or more of: a carbon source for the cells (e.g., methane, ethanol, acetate), a nitrate source (e.g., a nitrate mineral salt), a copper salt, e.g., $CuCl_2$. In some aspects, the kit comprises one or more containers, e.g., vials, flasks, tubes, bottles, plates, dishes, and the like. In some aspects, the instructions for using the materials of the kit in accordance with the one or more of the uses below. For example, the instructions in some aspects include instructions for culturing the cells and/or instructions for reducing the concentration of a metal atom, chlorinated compound, methanol, acetate, or ethanol from a system. Suitable methods of culturing the cells and/or instructions for reducing the concentration of a metal atom, chlorinated compound, methanol, acetate, or ethanol from a system are described herein.

Use

The present disclosures furthermore provide methods of using the compounds, complexes, conjugates, cells, cultures, and/or compositions described herein.

For example, a method reducing the concentration of a metal atom from a system is provided. The method comprises contacting the system with a compound, conjugate, cell, culture, or composition of the present disclosures, such that one or more metal atom-compound complexes (complexes comprising the compound bound to the metal atom) form in the system, and optionally removing the metal atom-compound complexes from the system. The metal atom may be any of the metals described herein, including the transition metals: gold, cadmium, cobalt, chromium, copper, iron, mercury, nickel, zinc, silver, lead, aluminum, manganese, uranium, or a combination thereof. In some aspects, the metal atom is selected from the group consisting of: Au(III), Cd(II), Co(II), Cr(VI), Cu(I), Cu(II), Fe(II), Fe(III), Hg(I), Hg(II), Ni(II), and Zn(II), Ag(I), Pb(II), Pb(IV), Al(III), Mn(II), Mn(III), Mn(IV), Mn(VI), Mn(VII), U(IV), U(VI), or a combination thereof. In some aspects, the metal atom is a copper atom.

The method in some aspects comprises removing the complexes from the system. Suitable means of removing metal-bound compounds are known in the art. In some aspects, the method comprises one or more steps which achieve the removal of the complexes from the system based on size, mass, polarity, or other chemical or physical features of the complex, which is different from the metal and from the compound (in unbound form). In this regard, the method in some aspects comprises one or more chromatography steps, filtration steps, centrifugation steps, and the like. The one or more chromatography steps in some embodiments comprises column chromatography, planar chromatography, displacement chromatography, gas chromatography, liquid chromatography, affinity chromatography, ion exchange chromatography, size exclusion chromatography, reversed-phase chromatography, two dimensional chromatography, simulated moving bed chromatography, pyrolysis gas chromatography, fast protein liquid chromatography, countercurrent chromatography, paper chromatography, thin layer chromatography, and/or chiral chromatography. The one or more chromatography steps in some aspects comprise the use of antibodies and/or magnetic beads.

The present disclosures furthermore provide a method of reducing the concentration of a chlorinated compound from a system. The method comprises contacting the system with the cell, the culture, or the composition of the present disclosures under conditions to reduce the concentration of a chlorinated compound from the system. In some aspects, the chlorinated compound is a carcinogenic compound. In some aspects, the chlorinated compound is a chlorinated ethene. Chlorinated ethenes are toxic substances which are widely distributed groundwater contaminants and are persistent in the subsurface environment. Reports on the biodegradation of these compounds under anaerobic conditions which might occur naturally in groundwater show that these substances degrade very slowly, if at all. Previous attempts to degrade chlorinated ethenes aerobically have produced conflicting results (Fogel et al., *Applied and Environmental Microbiology* 51(4): 720-

724 (1986)). In some aspects, the chlorinated ethene is trichloroethylene, cis-dichloroethylene, trans-dichloroethylene, or vinyl chloride.

In some aspects, the method of reducing the concentration of a chlorinated compound from a system comprises steps of degrading a chlorinated compound, as described herein at Example 2. In exemplary embodiments, the method comprises contacting a system comprising a chlorinated compound with a culture of *Methlocystis* strain SB2 and culturing the cells for greater than 50 hours (e.g., greater than 60 hours, greater than 70 hours, greater than 80 hours, greater than 90 hours, greater than 95 hours, greater than 97 hours). In some aspects, the SB2 cells are cultured on methane or acetate or ethanol.

The present disclosures moreover provide a method of reducing the concentration of methane, ethanol, or acetate from a system. The method comprises contacting the system with the cell, the culture, or the composition of the present disclosures under conditions to reduce the concentration of methane, ethanol or acetate from the system.

With regard to the methods described herein, in which cells or cultures thereof are contacted with a system, in some embodiments, the cells, e.g., SB2 cells, are cultured in conditions that support the growth and viability of the cells. For example, in some embodiments, the cells, e.g., SB2 cells, are cultured at a temperature below or about 37 degrees C. (e.g., below or about 36 degrees C., below or about 35 degrees C., below or about 34 degrees C., below or about 33 degrees, C, below or about 32 degrees C., below or about 31 degrees C.) and above or about 8 degrees C. (e.g., above or about 9 degrees C., above or about 10 degrees C.). In some aspects, the SB2 cells are cultured between about 10 and about 30 degrees C. (e.g., about 10 degrees C., about 11 degrees C., about 12 degrees C., about 13 degrees C., about 14 degrees C., about 15 degrees C. about 16 degrees C., about 17 degrees C., about 18 degrees C., about 19 degrees C., about 20 degrees C., about 21 degrees C., about 22 degrees C., about 23 degrees C., about 24 degrees C., about 25 degrees C., about 26 degrees C., about 27 degrees C., about 28 degrees C., about 29 degrees C., about 30 degrees C.).

In some embodiments, the cells, e.g., SB2 cells, are cultured at a pH between about 6 and 9 (e.g., about pH 5.8, about pH 5.9, about pH 6.0, about pH 6.1, about pH 6.2, about pH 6.3, about pH 6.4, about pH 6.5, about pH 6.6, about pH 6.7, about pH 6.8, about pH 6.9, about pH 7.0, about pH 7.1, about pH 7.2, about pH 7.3, about pH 7.4, about pH 7.5, about pH 7.6, about pH 7.7, about pH 7.8, about pH 7.9, about pH 8.0, about pH 8.1, about pH 8.2, about pH 8.3, about pH 8.4, about pH 8.5, about pH 8.6, about pH 8.7, about pH 8.8, about pH 8.9, about pH 9.0).

In some embodiments, the cells, e.g., SB2 cells, are cultured in medium comprising methane, acetate, ethanol, or a combination of two or all of the foregoing. In some embodiments, the cells, e.g., SB2 cells are cultured in medium comprising copper (e.g., medium comprising $CuCl_2$). In alternative embodiments, the cells, e.g., SB2 cells are cultured in medium lacking copper (e.g., medium lacking $CuCl_2$). In some embodiments, the cells, e.g., SB2 cells, are cultured in medium comprising nitrate (e.g., nitrate mineral salt). Also, in some aspects, the cells, e.g., SB2 cells, are shaken (e.g., at 225 rpm) during culturing.

In some embodiments, the cells, e.g., SB2 cells, are cultured in conditions which support the function or activity of a methane monooxygenase, e.g., a pMMO. In exemplary embodiments, the conditions lack the presence of any inhibitors of the methane monooxygenase, e.g., acetylene.

In some aspects, contacting the system with cells or cultures thereof of the present disclosures comprises culturing the cells in the system in accordance with the teachings of Example 1 and/or Example 2.

For purposes herein, the term "reduce" as well as words stemming therefrom, as used herein, do not necessarily imply a 100% or complete reduction. Rather, there are varying degrees of reduction of which one of ordinary skill in the art recognizes as having a potential benefit. In this respect, the methods of the present disclosures can provide any degree, extent, or level of reduction of the concentration of a metal atom, a chlorinated compound, or methane, acetate, or ethanol from a system. Accordingly, a reduction of about 5% or more, about 10% or more, about 20% or more, about 30% or more, about 40% or more, about 50% or more, about 60% or more, about 70% or more, about 75% or more, about 80% or more, about 90% or more, about 95% or more, about 98% or more, about 99% or more, or nearly 100% of the concentration of a metal atom, a chlorinated compound, or methane, acetate, or ethanol from a system is contemplated herein.

The present disclosures further provide a method of producing a nanoparticle comprising a metal atom. The method comprises incubating a solution comprising a metal atom with a compound, complex, conjugate, cell, culture, or composition of the present disclosures under conditions to form a nanoparticle comprising a metal atom. In some aspects, the nanoparticle comprises a metal selected from the group consisting of gold, cadmium, cobalt, chromium, copper, iron, mercury, nickel, rhodium, platinum, palladium, zinc, silver, lead, aluminum, manganese, uranium, or a combination thereof. In some aspects, the metal atom is selected from the group consisting of: Au(III), Cd(II), Co(II), Cr(VI), Cu(I), Cu(II), Fe(II), Fe(III), Hg(I), Hg(II), Ni(II), and Zn(II), Ag(I), Pb(II), Pb(IV), Al(III), Mn(II), Mn(III), Mn(IV), Mn(VI), Mn(VII), U(IV), U(VI), or a combination thereof. In some aspects, the metal atom is a gold, rhodium, platinum, or palladium atom.

The present disclosure provides a method for oxidizing water. The method comprises incubating a solution comprising a metal atom with a compound, complex, conjugate, cell, culture, or composition of the present disclosures under conditions effective and sufficient to oxidize water. In some aspects, the metal atom is selected from the group consisting of gold, cadmium, cobalt, chromium, copper, iron, mercury, nickel, rhodium, platinum, palladium, zinc, silver, lead, aluminum, manganese, uranium, or a combination thereof. In some aspects, the metal atom is selected from the group consisting of: Au(III), Cd(II), Co(II), Cr(VI), Cu(I), Cu(II), Fe(II), Fe(III), Hg(I), Hg(II), Ni(II), and Zn(II), Ag(I), Pb(II), Pb(IV), Al(III), Mn(II), Mn(III), Mn(IV), Mn(VI), Mn(VII), U(IV), U(VI), or a combination thereof. In specific embodiments, the compound preferentially binds to copper, inasmuch as some type 1 copper sites in proteins, e.g., ceruloplasmin, are known to have extraordinarily high reduction potentials (>1.0V) (Machonkin, et al., 1998; Li, et al., 2004). Such a high-potential site is believed to be able to oxidize water, which has a reduction potential of ~0.8V.

Systems

With regard to the present disclosures, the system may be any kind of open or closed system. For example, a closed system can be a liquid system and in some embodiments is a naturally occurring body of water (e.g., stream, lake, sea, ocean, river, pond, marsh, swamp, etc.). Alternatively, an open system can be a gaseous system, such as, for example, the atmosphere. In some aspects, the atmosphere is within close proximity to a landfill or an animal feeding operation.

In some aspects, the system, e.g., the liquid system or gaseous system, is a contaminated or polluted system, in which the system is unfit for its intended use and/or comprises chemicals (e.g., gaseous or liquid pollutants) which are harmful to living organisms, e.g., humans, animals, plants, etc. In some aspects, the pollutant of the system is methane, a chlorinated compound (e.g., chlorinated ethene (e.g., trichloroethylene, cis-dichloroethylene, trans-dichloroethylene, vinyl chloride), a metal (e.g., mercury, lead, zinc, iron, copper, cadmium, chromium, nickel, aluminum), a component of raw sewage (e.g., urine, feces), a fertilizer (e.g., phosphate fertilizer), an insecticide, an herbicide, a petroleum hydrocarbon, an oil, a grease, a radioactive substance, or heat.

The following examples are given merely to illustrate the present invention and not in any way to limit its scope.

EXAMPLES

Example 1

Characterization of a Novel Facultative *Methylocystis* Strain Capable of Growth on Methane, Acetate, or Ethanol A non-motile strain of *Methylocystis*, strain SB2, isolated from a spring bog in southeast Michigan had a curved rod morphology with a typical type II intracytoplasmic membrane system. This organism expressed the membrane-bound or particulate methane monooxygenase (pMMO) as well as a chalkophore with high affinity for copper and did not express the cytoplasmic or soluble methane monooxygenase (sMMO). Strain SB2 was found to grow within the pH range of 6-9, with optimal growth at 6.8. Growth was observed at temperatures ranging between 10 and 30° C., with no growth at 37° C. The DNA G+C content was 62.9 mol %. Predominant fatty acids were 18:1ω7c (72.7%) and 18:1ω9c (24%) when grown on methane. Phylogenetic comparisons based on both pmoA and 16S rRNA sequences indicated that this organism belonged to the *Methylocystis* genus, and was closely related to *Methylocystis rosea* SV97$^T$ and *Methylocystis echinoides* IMET 10491$^T$ (98% 16S rRNA gene sequence similarity to both strains). DNA:DNA hybridizations indicated that strain SB2 had 70% similarity with *Methylocystis rosea* SV97$^T$. Unlike *M. rosea* SV97$^T$, strain SB2 was able to utilize not only methane for growth, but also ethanol and acetate. Furthermore, the predominant fatty acids in strain SB2 were different from those found in *M. rosea* SV97$^T$, i.e., 54.2% and 39.7% of fatty acids are 18:1ω8 and 18:1ω7 in *M. rosea* SV97$^T$, while 18:1ω8 is completely absent in strain SB2.

Methanotrophs, organisms that consume methane as their sole source of carbon and energy, are found in a wide variety of environments where methane:air interfaces develop, including forest and agricultural soils, wetlands, landfills, geothermal areas (e.g., hot springs), marine and freshwater sediments, amongst other locations. Most methanotrophs are physiologically and phylogenetically distinct organisms in either the γ-Proteobacteria (Type I methanotrophs) and α-Proteobacteria (Type II methanotrophs) (Semrau, et al., 2010), although recently methanotrophs from Verrucomicrobia have been found (Dunfield, et al., 2007; Islam, et al., 2008; Pol, et al., 2007).

Four genera have been identified within Type II methanotrophs, specifically *Methylocystis* and *Methylosinus* (within the Methylocystaceae family) and *Methylocapsa* and *Methylocella* (within the Beijierinckiacaea family). Most of these bacteria are obligate methanotrophs, i.e., can only grow on $C_1$ substrates, although *Methylocella* spp. are facultative, being able to grow on a variety of organic acids (Dedysh, et al., 2005). These acidophilic organisms, growing between pH 4.5-7 (Dunfield, et al., 2003) only express sMMO (Dedysh, et al., 2000; Dunfield, et al., 2003). *Methylocapsa aurea* KYG$^T$ has been isolated from a forest soil that is also facultative, being able to grow on acetate, but expresses only pMMO. This organism had an optimal growth pH of 6.0-6.2 (Dunfield, et al., 2010). Recently, facultative methanotrophs able to grow on acetate have been reported in the *Methylocystis* genus, specifically the moderate acidophiles *Methylocystis* strain H2s and *M. heyeri* H2$^T$, and the mesophile *M. echinoides* IMET10491$^T$, (Belova, et al, 2010). Here we describe the isolation and characterization of another facultative mesophilic methanotroph, strain SB2, able to grow on methane, acetate or ethanol, that is a novel member of *Methylocystis*.

Isolation of Strain SB2: Strain SB2 was isolated from a spring bog located near Ann Arbor, Mich. (N 42° 16' 13.7", W 83° 39' 36.5") in July 2006. Aqueous samples were spread onto nitrate mineral salts (NMS) Bacto-agar plates (Whittenbury, et al., 1970). Plates were incubated with a $CH_4$/air mixture (1:2) at 30° C. Single colonies were selected from plates and continuously re-streaked onto fresh NMS plates and nutrient agar plates until no growth on nutrient agar was observed. Culture purity was confirmed using phase-contrast and electron microscopy. To further verify isolate purity, DNA was extracted from methane-grown organisms and 16S rRNA genes amplified via PCR and cloned using the TA cloning kit. Fifty recombinant clones of 16S rRNA gene PCR products were obtained and at least 1000 bp sequenced per clone, with all clones found to have identical sequences. Once pure cultures were obtained, the cultures were maintained by transferring to fresh plates at least once a month.

Figure 2:
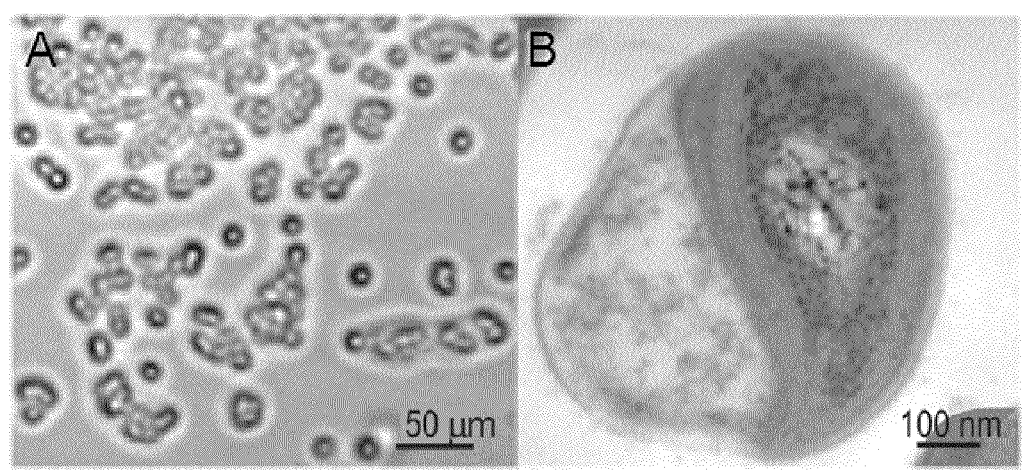
FIG. 2 represents a phase contrast (A) and transmission electron micrographs (B) of *Methylocystis* strain SB2 grown on methane. For TEM image acquisition, *Methylocystis* strain SB2 was incubated in liquid NMS (Whittenbury et al., 1970) supplemented with 10 µM of copper as $CuCl_2$ for two days, and then harvested by centrifugation at 12000 rpm for 10 min at 4° C. The sample was fixed in 2.5% glutaraldehyde in 0.1 M Sorensen's buffer, postfixed in 1% osmium tetroxide in the same buffer, and then stained with uranyl acetate and lead citrate. The sections were examined using a Philips CM100 electron microscope (Philips/I-EI, Hillsboro, Oreg.) at 60 kV. Images were recorded digitally using a Hamamatsu ORCA-HR digital camera system operated using AMT software (Advanced Microscopy Techniques Corp., Danvers, Mass.). 80×36 mm (600×600 DPI)

Characterization of Strain SB2: On NMS agar without copper, strain SB2 formed round, convex, red-orange-pigmented colonies. When SB2 was spread onto NMS agar with 10 or 40 µM copper (as $CuCl_2$), colonies were initially white-colored, but darkened over time (see FIG. 1). Interestingly, strain SB2 grew in liquid cultures in the absence of copper with methane as the carbon source in NMS medium, but grew better in the presence of copper. Vitamins were also not required for growth. Strain SB2 was found to be Gram-negative and non-motile. Staining for *Azotobacter*-type cysts was negative using standard procedures (Vela & Wyss, 1964), and neither exospores nor rosettes were observed after a 4 week incubation. Phase-contrast micrographs showed that they create large and tight aggregates of cells surrounded by a capsule (FIG. 2A). Electron microscopy showed that SB2 cells were 0.7-1.0 µm wide and 0.9-2.0 µm in length when grown on methane with a well developed system of type II intracytoplasmic membranes aligned parallel to the cytoplasmic membrane (FIG. 2B). Inclusions of low electron density were also occasionally observed, possibly comprising poly-β-hydroxyalkanoate granules. The DNA G+C content was measured to be 62.9 mol % as determined by DSMZ (Brausnchwieg, Germany) using standard protocols (Cashion, et al., 1977; Mesbah, et al., 1989; Tamaoka & Komagata, 1984). Predominant fatty acids were 18:1ω7c (72.7%), 18:1ω9c (24%), and 16:1ω7c (2.2%) when strain SB2 was grown on methane as determined by Microbial Insights, Inc. (Rockford, Tenn.).

Figure 3:
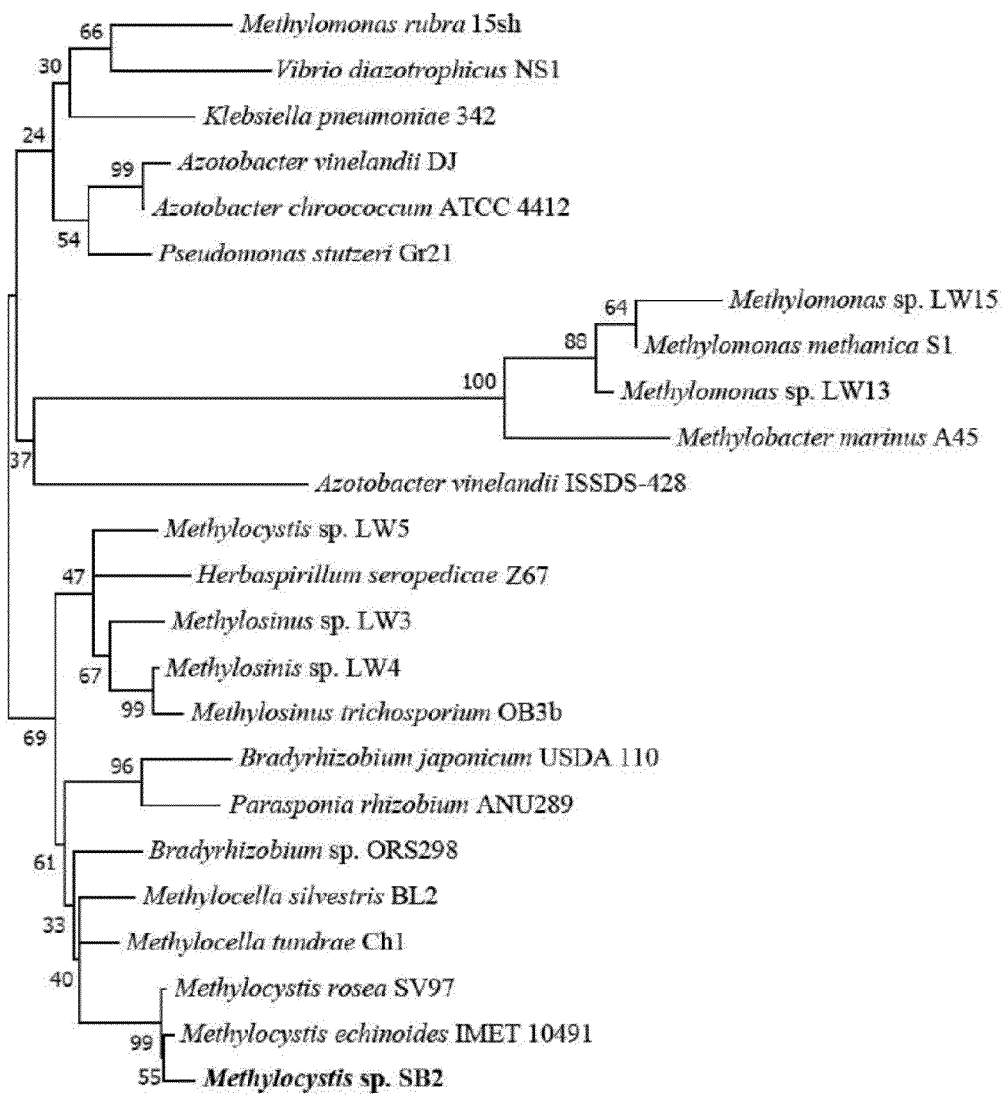
FIG. 3 represents a graph of the phylogenetic relationship of the nifH gene sequence of *Methylocystis* strain SB2 with other methanotrophs. The evolutionary history was inferred using the Neighbor-Joining method. Phylogenetic analyses were conducted in MEGA4 (Tamura et al., 2007). Scale bar indicates 0.1 changes per nucleotide position.
Figure 4:
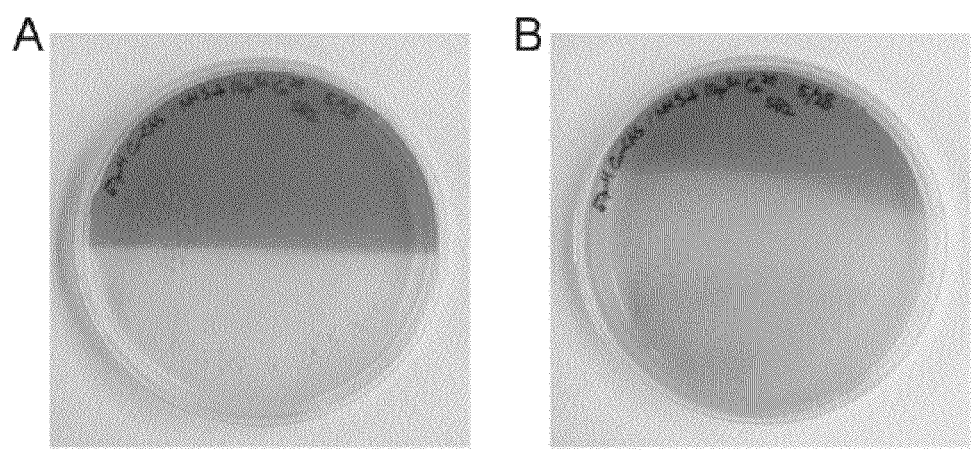
FIG. 4 represents split NMS/50 µM Cu-CAS plates for detection of chalkophore production over time by *Methylocystis* strain SB2. (A). *Methylocystis* strain SB2 incubated for 6 days at 30° C. (B) *Methylocystis* strain SB2 incubated for 21 days at 30° C. NMS agar was supplemented with 1 µM copper as $CuCl_2$. Fifty micromolar Cu-CAS agar was prepared by adding 50 ml of 1.05 mM CAS solution to 10 ml of a 5 mM $CuCl_2$ solution. This solution was then added to 40 ml of 2.625 mM HDTMA under stirring to give final concentrations of 0.5 mM, 0.525 mM and 1.05 mM of Cu, CAS and HDTMA respectively. 450 ml of NMS was prepared separately. Concentrations of salts were adjusted for 500 ml NMS medium, considering later addition of the Cu-CAS solution. The purple-colored Cu-CAS stock solution and NMS agar preparation were then autoclaved separately. After cooling to ~50° C., 50 ml of the purple-colored Cu-CAS solution was carefully pippetted into NMS agar medium. Vitamin and phosphate buffer solutions were then added to the medium. After the agar plates cooled and solidified, half of the agar gel was carefully excised with a heat-sterilized razor. The empty space was then filled with sterilized NMS agar. 80×37 mm (600×600 DPI)

Strain SB2 grew at pH values ranging from 6 to 9 with methane as the carbon and energy source, with optimum growth at 6.8 when grown on methane in NMS medium. Growth on methane was also observed at temperatures ranging from 10 to 30° C., but no growth was observed at 37° C. Many nitrogen sources were tested with methane as the carbon source: nitrate (as potassium nitrate), ammonia (as ammonium chloride), L-alanine, L-serine, L-isoluecine, L-proline, L-methionine, L-glutamine, L-asparagine, L-lysine, L-glycine, L-histidine, and L-arginine. Of these, strain SB2 was able to utilize nitrate, ammonium, L-isoleucine, L-proline, and L-glutamine as nitrogen sources, and was able to grow poorly in nitrogen-free mineral medium. The presence of nifH was confirmed using PCR using specific primers for nifH (Auman, et al., 2001; Zehr & McReynolds, 1989). Sequencing of the nifH PCR product showed high similarity to nifH from *Methylocystis rosea* SV97T and *Methylocystis echinoides* IMET 10491$^T$ (see FIG. 3). Furthermore, strain SB2 grew from an initial $OD_{600}$ of 0.037 to 0.12 after three days in nitrogen-free medium with methane as the carbon source (P<0.01). Collectively, these data indicate that strain SB2 can fix nitrogen. Finally, a recent plate assay developed for the screening of methanotrophs for chalkophore production. i.e., copper-binding compounds analogous to siderophores, (Yoon, et al., 2010) indicated that strain SB2 did produce a chalkophore (see FIG. 4).

PCR amplification of functional genes of the particulate methane monooxygenase (pmoA, encoding for the α-subunit of pMMO) using A189-mb661 (Costello & Lidstrom, 1999) revealed the presence of pMMO. Similar PCR assays using mmoXA-mmoXB (Auman et al., 2000), mmoXf882-mmoXr1403 (McDonald et al., 1995), and mmoX206f-mmoX886r (Hutchens et al., 2004) failed to yield any PCR products for mmoX (encoding for the α-subunit of the sMMO hydroxylase). The lack of sMMO was also indicated by negative results of the naphthalene assay, specific for sMMO activity (Brusseau, et al, 1990) in either the absence or presence of copper.

Growth of strain SB2 on Alternative Carbon Sources: Growth on methanol (0.05% v/v) and methylamine, glucose, fructose, sucrose, galactose, xylose, arabinose, and maltose (all at a concentration of 0.05% w/v) was tested, as were the organic acids formate, pyruvate, succinate, malate, citrate and oxalate (all added as sodium salts at a concentration of 0.05% w/v). No growth was observed on any of these substrates. Some methanotrophs can utilize methanol as well as methane, but many methanotrophs have been shown to be unable to grow on methanol either due its toxicity or the toxicity associated from the accumulation of formaldehyde from methanol oxidation (Best and Higgins, 1981; Cornish et al. 1984; Linton and Vokes, 1978; Whittenbury, et al., 1970; Wilkinson, et al., 1974). Here, the ability of strain SB2 to grow on methanol was tested at concentrations ranging from 0.01-1% (v/v), with no growth observed under any concentration.

Figure 5:
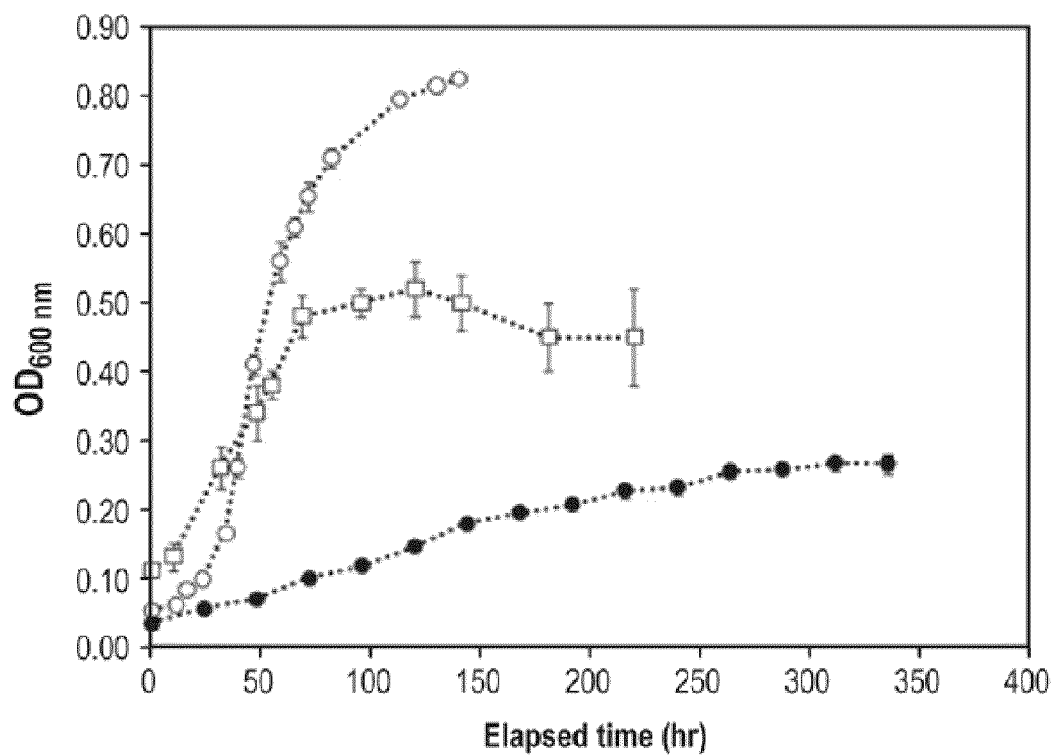
FIG. 5 represents a graph demonstrating the growth of *Methylocystis* strain SB2 on various carbon sources: ○=methane (10% v/v in the headspace); ●=acetate (0.1% w/v); □=ethanol (0.1% v/v). Error bars indicate the range of duplicate samples. *Methylocystis* strain SB2 was incubated in 50 ml of NMS medium in 250 ml flask supplemented with 10 µM of copper as $CuCl_2$. The flasks were incubated at 30° C. with shaking at 250 rpm. Cell growth was monitored by measuring $OD_{600}$ using a Spectronic-20 (Milton Roy Company, USA). Error bars indicate the range of duplicate samples. Where error bars are not apparent, the symbol size is greater than the measured range. The initial pH of the growth medium was 6.8 for all substrates, and after reaching the stationary phase, the pH was 6.7 for all substrates. 196×138 mm (600×600 DPI)

Strain SB2 grew, however, on either acetate (as sodium acetate) or ethanol when the growth concentrations of these substrates were varied between 0.01-0.5% (w/v) and 0.05 and 1% (v/v), respectively. Optimal growth for both ethanol and acetate occurred at 0.1% (v/v and w/v, respectively) with nitrate added as the nitrogen source (FIG. 5). Growth on methane and ethanol followed standard exponential kinetics, with growth rates of 0.052±0.004 h$^{-1}$ and 0.022±0.002 h$^{-1}$ for methane and ethanol, respectively. Strain SB2 grew to a higher $OD_{600}$ on methane than on ethanol (0.83 and 0.45, respectively). Growth on acetate, however, was slower, and could be modeled as either exponential or linear growth, to a final $OD_{600}$ of 0.26. The possible linear growth on acetate is intriguing, and may be due to the pH of the growth medium, 6.8. At this pH, 99% of the added acetate exists as the dissociated form. It is believed that undissociated acetate is transferred across the cell membrane, thus the proton motive force is dissipated to transport acetate into the cell (Axe and Bailey, 1995), which inhibits microbial growth. It is interesting to note that other methanotrophs shown to be able to grow better on acetate, e.g., *Methylocapsa aureus, Methylocella silvestris*, and *Methylocystis* sp. H2s, grow optimally at lower pH values (Dunfield, et al., 2010; Dedysh, et al., 2005; Belova, et al., 2010) where more of the acetate exists in the undissociated form, while *Methylocystis echinoides* IMET 10491$^T$, also recently found to grow on acetate on standard NMS medium, which has a pH of 6.8, does so relatively poorly (Belova, et al., 2010). Furthermore, the growth yield and carbon conversion efficiency of *Methylocystis* strain SB2 and *Methylocella silvestris* BL2 on methane were similar, but *Methylocella silvestris* BL2 exhibited greater yield and carbon efficiency on acetate than *Methylocystis* strain SB2 (see Table 1).

TABLE 1

Growth yield and carbon conversion efficiency of *Methylocystis* strain SB2 and *Methylocella silvestris* BL2 grown on methane and acetate.

| Strain | Substrate | Growth yield [(g cell dry weight ■(mol substrate$^{-1}$] | Efficiency of carbon conversion [%] | Reference |
| --- | --- | --- | --- | --- |
| *Methylocystis* strain SB2 | Methane | 3.13 (±0.12) | 12.3 (±0.5) | This study |
| *Methylocella silvestris* BL2 | | 3.59 (±0.104) | 13.2 (±0.698) | Dedysh, et al. (2005) |
| *Methylocystis* strain SB2 | Acetate | 12.0 (±0.13) | 22.1 (±0.2) | This study |
| *Methylocella silvestris* BL2 | | 20.5 (±1.24) | 40.1 (±2.43) | Dedysh, et al. (2005) |

For Table 1, the molar growth yield (g dry cell■(mol substrate$^{-1}$)) and the efficiency of carbon conversion to cell material (g cell carbon■(g substrate carbon)$^{-1}$) were determined in triplicate 5 ml of NMS medium supplemented with 10 μM of copper as CuCl2 using specially constructed 32.5 ml vials containing a $CH_4$/air mixture (1:2 ratio in the headspace), or 0.10% (w/v) of sodium acetate as a sole carbon source. $CH_4$ and acetate concentrations were measured using gas chromatography equipped with a FID (HP 5890 Series II) and ion chromatography (Dionex DX100, Sunnyvale, Calif.), respectively. Cell growth was monitored by measuring $OD_{600}$ using a Spectronic-20 spectrometer (Milton Roy Company, USA). Turbidity was correlated to protein concentration using the Bio-Rad Protein Assay (Bio-Rad Laboratories, Richmond, Calif.) with bovine serum albumin (BSA) as the standard following manufacturer's instructions. To estimate the carbon content of biomass it was assumed that dry biomass was 50% protein, and $C_4H_8O_2N$ was the biomass elemental composition (Leak and Dalton, 1986). Numbers in parentheses give the standard error of measurements.

Figure 6:
FIG. 6 is an micrograph of strain SB2 grown on ethanol, obtained using a transmission electron microscope.

The purity of cultures grown on ethanol and acetate was verified by plating on nutrient agar, with no growth observed after incubation for 4 weeks. DNA was extracted from ethanol- and acetate-grown organisms with 16S rRNA genes amplified via PCR and cloned. 50 recombinant clones of 16S rDNA PCR products were obtained for both ethanol- and acetate-grown organisms and at least 1000 bp sequenced per clone. All clones found to have identical sequence as to that for methane-grown cultures, verifying culture purity. Transmission electron micrographs of strain SB2 grown on ethanol confirmed the presence of intracytoplasmic membranes aligned parallel to the cytoplasmic membrane, as well as inclusions of low electron density, possibly poly-β-hydroxybutyrate granules (see FIG. 6).

As mentioned earlier, other *Methylocystis* strains have been recently found to grow on acetate, including the moderate acidophiles *Methylocystis heyeri* H2$^T$, *Methylocystis* strain H2s, and the mesophile *Methylocystis echinoides* IMET10491$^T$, but not *Methylocystis rosea* SV97$^T$ (Belova, et al., 2010; Wartiainen, et al., 2006). The growth of *Methylocystis echinoides* IMET10491$^T$ and *Methylocystis heyeri* H2$^T$ on acetate, however, was less than that observed here for strain SB2, which was more similar to that found for *Methylocystis* strain H2s and *Methylocapsa aurea* KYG$^T$ (Belova, et al., 2010), i.e., max OD$_{410}$ of 0.09 for *Methylocystis echinoides* IMET10491$^T$, max OD$_{410}$ of 0.14 for *Methylocystis heyeri* H2$^T$, max OD$_{410}$ of ~0.23 for *Methylocystis* strain H2s, max OD$_{600}$ of 0.3 for *Methylocapsa aurea* KYG$^T$, and a max OD$_{600}$ of 0.26 for strain SB2.

Figure 7:
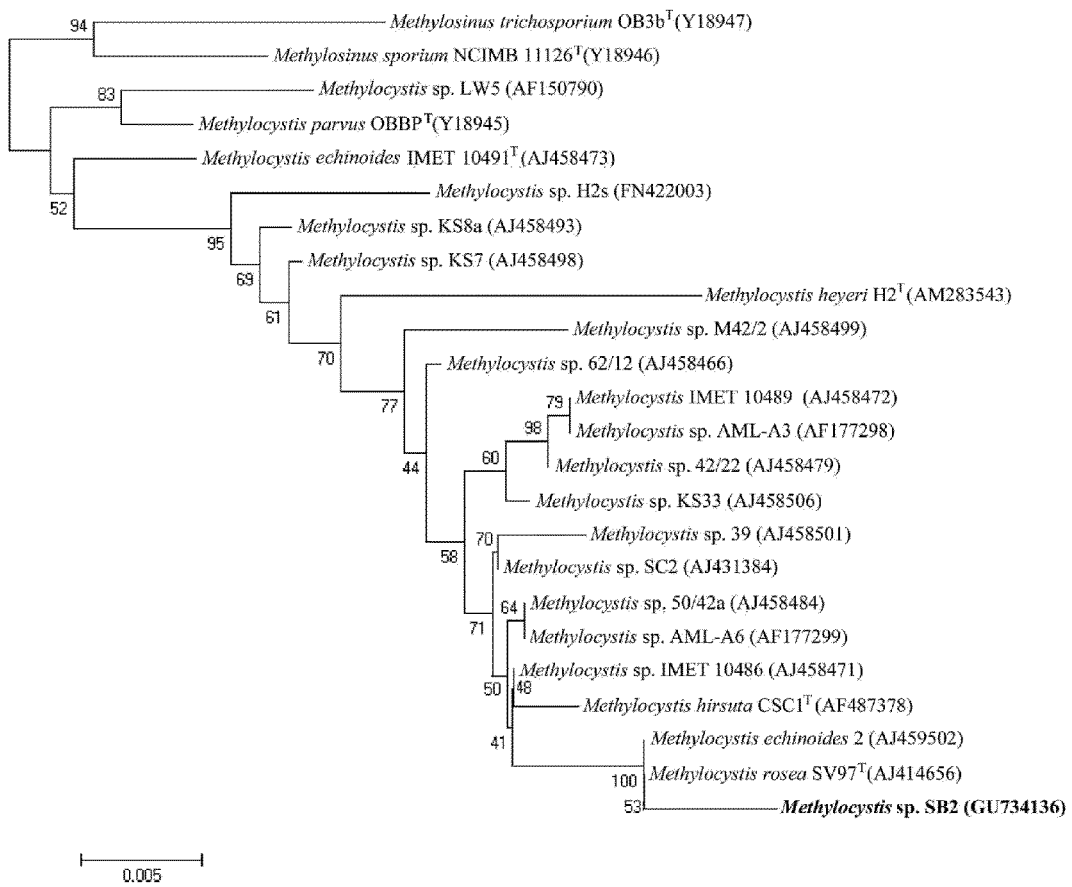
FIG. 7 represents a graph of the phylogenetic relationship of the 16S rRNA gene sequence of *Methylocystis* strain SB2 with other methanotrophs. The evolutionary history was inferred using the Neighbor-Joining method based on nucleotide sequences of partial 16S rDNA genes (Saitou and Nei, 1987). Bootstrap values derived from 100 replicates are shown. Phylogenetic analyses were conducted in MEGA4 (Tamura et al., 2007). Scale bar indicates 0.005 changes per nucleotide position. 168×132 mm (600×600 DPI)
Figure 8:
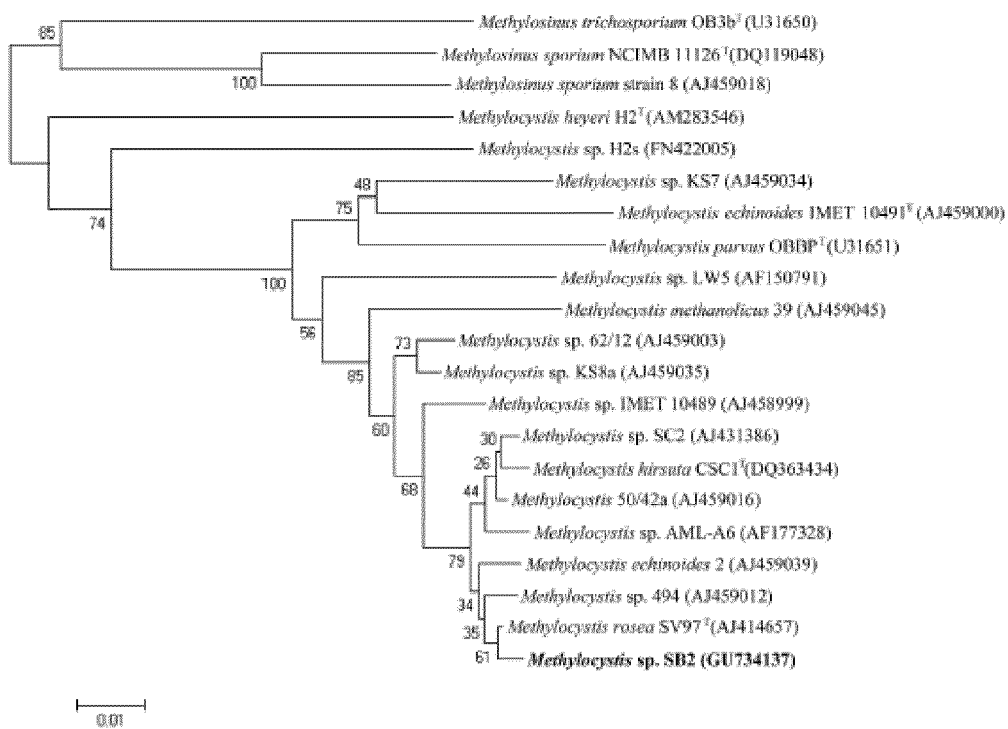
FIG. 8 represents a graph of the phylogenetic relationship of the pmoA gene sequences of *Methylocystis* strain SB2 with other methanotrophs. Neighbor-Joining method (Jukes-Cantor correction, Jukes-Cantor, 1969) was used, and bootstrap values derived from 100 replicates are shown. Phylogenetic analyses were conducted in MEGA4 (Tamura et al., 2007). Scale bar indicates 0.01 changes per nucleotide position. 168×124 mm (600×600 DPI)

Phylogenetic comparison of strain SB2 with other methanotrophs: The 16S rRNA sequence (1132 bp, GenBank accession number GU734136 (SEQ ID NO: 1)) of strain SB2 was found to be most similar to *Methylocystis rosea* SV97$^T$ (98%) and *Methylocystis echinoides* IMET 10491$^T$ (98%)(see FIG. 7). Lower similarity values were found with *Methylocystis parvus* OBBP$^T$ (94%), as well as with *Methylosinus trichosporium* OB3b$^T$ (94%) and *Methylosinus sporium* NCIMB 11126$^T$ (95%). Using a neighbor joining analysis, strain SB2 clustered very closely with *Methylocystis rosea* SV97$^T$ based on nucleotide sequences of partial 16S rDNA genes. Similar patterns were observed with pmoA sequences (437 bp; Genbank accession number GU734137 (SEQ ID NO: 2)), with strain SB2 having 99% similarity to pmoA from *Methylocystis rosea* SV97$^T$, 98% similarity to pmoA from *Methylocystis echinoides* IMET 10491$^T$, 94% similarity to *Methylocystis parvus* OBBP$^T$, and 87% similarity to pmoA from both *Methylosinus trichosporium* OB3b$^T$ and *Methylosinus sporium* NCIMB 11126$^T$ (see FIG. 8). Phylogenetic analysis based on partial pmoA sequence data supported the placement of strain SB2 within the *Methylocystis* genus of the α-Proteobacteria. Given the highest similarity between strain SB2 and *Methylocystis rosea* SV97$^T$ for both 16s rRNA and pmoA gene sequences, DNA-DNA hybridizations were performed between these strains by DSMZ (Brausnchwieg, Germany) using 2×SSC buffer (0.3 M NaCl, 0.03M sodium citrate, pH 7.0) with 5% (v/v) formamide at a renaturation temperature of 70° C. It was found that strain SB2 had an average 70% DNA-DNA similarity with *Methylocystis rosea* SV97$^T$ from duplicate samples (range of 68.8-71.3%).

Although strain SB2 showed relatively high DNA-DNA similarity to *Methylocystis rosea* SV97$^T$ as well as high 16S rRNA sequence similarity, it can not be definitively declared as belonging to the same species as *Methylocystis rosea* SV97$^T$ given the recommendation of a threshold value of 70% DNA-DNA similarity for the definition of bacterial species by the ad hoc committee (Wayne et al., 1987). In such a situation, other physiological data must be considered, e.g., range of growth substrates, growth conditions, etc. As outlined in Table 2 below, there are significant differences between strain SB2 and *M. rosea* SV97$^T$ as well as with *Methylocystis echinoides* IMET 10491$^T$, which has been recently found to also grow on acetate.

TABLE 2

Characteristics distinguishing *Methylocystis* sp. SB2 from *Methylocystis rosea* SV97T and *Methylocystis echinoides* IMET 10491T

| Characteristic | *Methylocystis* sp. SB2 | *Methylocystis rosea* SV97$^T$ | *Methylocystis echinoids* IMET 1049$^T$ |
|---|---|---|---|
| Cell Morphology | Curved rods | Straight and curved rods | Coccibacilli/rods/vibroid |
| Pigmentation | Varies with copper concentration (white, pink, red, and brown) | Pink-red | White/buff |
| Spinae | − | − | + |
| Growth: | | | |
| 37° C. | − | + | −/+* |
| pH 5.0 | − | + | − |
| pH 9.0 | + | + | − |
| Acetate | + | − | + |
| Ethanol | + | − | ND |
| Predominant fatty acids | 18:1ω7c; 18:1ω9c; 16:1ω7c | 18:1ω8; 18:1ω7; 16:1ω7 | 18:1ω8; 18:1ω7; |
| DNA G + C content (mol %) | 62.9 | 62 | 62 |
| DNA-DNA Hybridization with SB2 (range of duplicate samples) | ND | 70 % (68.8-71.3) | ND |

ND = not determined;
* − conflicting findings reported in the literature (Lindner et al., 2007; Bowman et al., 1993)
Data for *Methylocystis rosea* SV97T are from Wartiainen et al., (2006) and data for *Methylocystis echinoides* IMET 10491T are from Bowman, et al., (1993), Lindner, et al., (2007), and Belova, et al., (2010).

Strain SB2 can grow on multi-carbon compounds while *Methylocystis rosea* SV97$^T$ can not. Additional differences between *Methylocystis rosea* SV97$^T$ and strain SB2 include the findings that strain SB2 can not grow either at 37° C., or below pH 6, that the pigmentation of strain SB2 varies with copper concentration, as well as large differences in the predominant fatty acids. Strain SB2 also is different from *Methylocystis echinoides* IMET 10491$^T$ in that strain SB2 lacks spinae, has variable red coloration, and has different predominant fatty acids. It is interesting to note that the predominant fatty acids in *Methylocystis rosea* SV97$^T$ and *Methylocystis echinoides* IMET 10491$^T$ are 18:1ω8 and 18:1ω7, while strain SB2 they are 18:1ω7c and 18:1ω9c, and that the presence of 18:1ω9c is rare in *Methylocystis* spp (Bowman, et al., 1993).

In summary, a novel facultative methanotroph, *Methylocystis* strain SB2, similar to both *Methylocystis rosea* SV97$^T$ and *Methylocystis echinoides* IMET 10491$^T$, was found that can utilize multi-carbon substrates for growth. At this time, it is unclear whether strain SB2 is a novel species or subspecies within *Methylocystis*, and this strain should be characterized further to resolve this issue, e.g., DNA:DNA hybridizations with other methanotrophs. The finding that strain SB2 can utilize multi-carbon compounds for growth supports the suggestion of Belova, et al. (2010) that some methanotrophs, particularly *Methylocystis* spp. utilize such compounds to generate reducing equivalents that enhance methanotrophic growth in situ, particularly in bogs where the concentration of acetate can be appreciable and acidic conditions can cause the undissociated form of acetate to predominate. Further work is warranted to determine how broadly distributed facultative methanotrophy is and what compounds other than ethanol and acetate can be utilized by these organisms.

Example 2

Constitutive Expression of pMMO by *Methylocystis* Strain SB2 when Grown on Multi-Carbon Substrates: Implication for Biodegradation of Chlorinated Ethenes The particulate methane monooxygenase (pMMO) in *Methylocystis* strain SB2, was found to be constitutively expressed in the absence of methane when the strain was grown on either acetate or ethanol. Real-time quantitative PCR and reverse transcription-PCR showed that the expression of pmoA decreased by one to two orders of magnitude when grown on acetate as compared to growth of strain SB2 on methane. The capability of strain SB2 to degrade a mixture of chlorinated ethenes in the absence of methane was examined to verify the presence and activity of pMMO under acetate-growth conditions as well determine the effectiveness of such conditions for bioremediation. It was found that when strain SB2 was grown on acetate and exposed to 40 µM each of trichloroethylene (TCE), trans-dichloroethylene (t-DCE), and vinyl chloride (VC), approximately 30% of VC and t-DCE was degraded but no appreciable TCE removal was measured after 216 hours of incubation. The ability to degrade VC and t-DCE was lost when acetylene was added, confirming that pMMO was responsible for the degradation of these chlorinated ethenes by *Methylocystis* strain SB2 when the strain was grown on acetate.

Methanotrophs are a group of bacteria that utilize methane as their sole source of carbon and energy. From both in situ experiments and studies with isolated laboratory strains, methanotrophs have been shown to degrade a wide range of chlorinated hydrocarbons, particularly chlorinated ethenes (Semprini et al., 1990; Tsien et al., 1989; Lee et al., 2006). In fact, methanotrophic-mediated oxidation of chlorinated ethenes has a comparative advantage over anaerobic biodegradation such as reductive dechlorination by *Dehalococcoides*, as methanotrophs more readily degrade smaller and more toxic compounds, i.e., trans-dichloroethylene (t-DCE) and vinyl chloride (VC) (Lee et al., 2006; Yoon and Semrau, 2008), which are often residual intermediates from anaerobic trichloroethylene (TCE) degradation (Maymo-Gatell et al., 1999).

The first step in the methane oxidation pathway, the conversion of methane to methanol, is mediated by the methane monooxygenase (MMO). Two forms of MMO are known, one in the cytoplasm or soluble fraction (soluble MMO or sMMO) and another in the membrane or particulate fraction (particulate MMO or pMMO). Most known methanotrophs only express pMMO, but some can express both forms. For these organisms, expression is regulated by the copper-to-biomass ratio: sMMO is expressed at very low copper-to-biomass ratio (<5.64 µmol Cu g$^{-1}$ protein) while pMMO expression is stimulated when copper is more abundant (Hanson and Hanson, 1996; Nielsen et al., 1997; Morton et al., 2000; Murrell et al., 2000; Choi et al., 2003; Semrau et al., 2010).

Both forms of the MMO have been shown to degrade chlorinated ethenes, including TCE, t-DCE, and VC (Lee et al., 2006; Scheutz et al., 2004; Van Hylckama Vlieg et al., 1996; Yoon and Semrau, 2008). pMMO-expressing organisms have a much higher specificity for methane than sMMO-expressing organisms, and thus, exhibit much slower kinetics towards non-methane substrates. As a result, it was initially believed that expression and activity of sMMO is essential for effective degradation of chlorinated hydrocarbons (Oldenhuis et al., 1989; Hanson and Hanson, 1996). Recent research, however, discovered that the activity of sMMO toward methane is severely inhibited when high concentrations (>50 µM) of TCE, t-DCE, and VC are present because of inhibition of methane consumption and the toxicity of the products of chlorinated ethene oxidation (Lee et al., 2006; Yoon et al., 2008). *Methylosinus trichosporium* OB3b expressing pMMO was, however, able to maintain viability and growth at elevated concentrations of chlorinated ethenes, while also degrading more of the chlorinated ethenes than sMMO-expressing organisms despite its comparatively slow kinetics (Lee et al., 2006; Yoon et al., 2008).

As methanotrophs were initially believed to only grow on methane, a continuous supply of methane was deemed necessary to ensure methanotroph-mediated biodegradation regardless of which form of MMO was expressed. This can act as a significant drawback for in situ biodegradation given the poor solubility of methane in water, slow mass-transfer of methane from the gas to liquid phase, and competition of methane with chlorinated solvents for binding to either form of MMO. The discovery of facultative methanotrophs (Belova et al., 2010; Dedysh et al., 2005; Dunfield et al., 2010; Im et al., submitted), however, indicates that methanotrophic degradation of chlorinated ethenes without methane might be possible, provided that either form of MMO is constitutively expressed and remains active in presence of the alternative growth substrate. In the case of *Methylocystis* sp. H2s, constitutive expression of pmoA was observed when the organism was grown in the presence of acetate and absence of methane (Belova et al., 2010). Chlorinated ethene degradation utilizing these facultative methanotrophs in the absence of methane, if possible, may be advantageous for in situ bioremediation strategies given the greater solubility of alternative growth substrates (e.g., acetate) and the lack of competition between the alternative growth substrate and various chlorinated ethenes for binding to the MMO.

In this example, we report the constitutive expression of pmoA by *Methylocystis* strain SB2 when this organism was grown on either acetate or ethanol in the absence of methane. Using real-time quantitative RT-PCR, we have quantified the expression of pmoA by *Methylocystis* strain SB2 when grown on either methane or acetate. To verify the presence of pMMO in *Methylocystis* strain SB2 when grown on acetate, we performed SDS-PAGE gel assays. To determine the usefulness of *Methylocystis* strain SB2 for biodegradation of chlorinated ethenes when grown on acetate, we examined the long-term degradation of a mixture of trichloroethylene (TCE), trans-dichloroethylene (t-DCE), and vinyl chloride (VC). After initial confirmation of degradation activity, a selective inhibitor of pMMO, acetylene, was used to verify that pMMO was responsible for the observed degradation when *Methylocystis* strain SB2 was grown on acetate.

Figure 9:
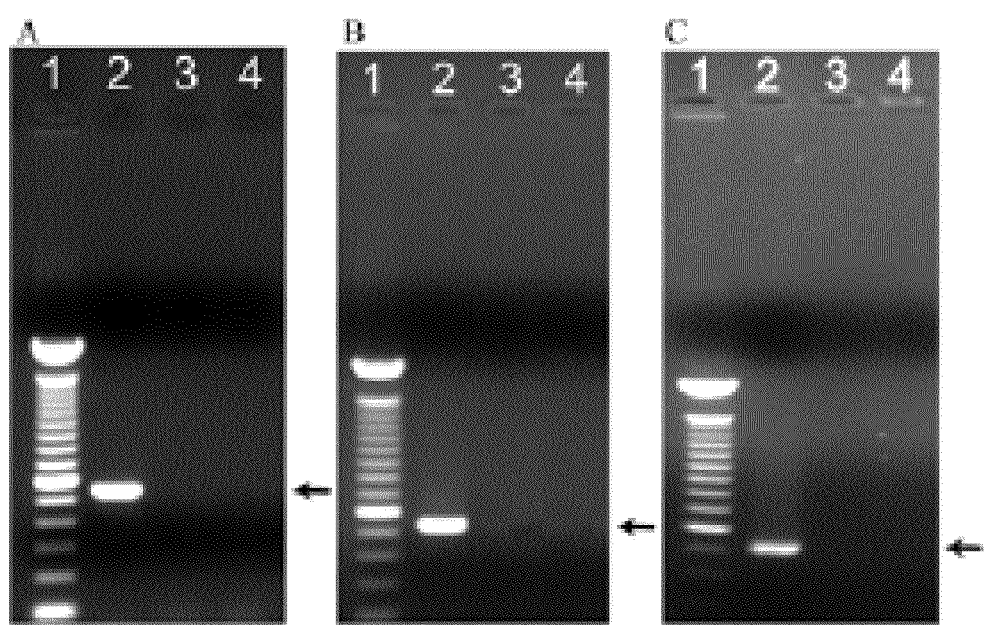
FIG. 9 shows the results of reverse transcription-polymerase chain reaction assays of pmoA expression of *Methylocystis* strain SB2 grown on NMS medium with 10 µM copper and either: (A) methane (15% v/v in the headspace); (B) ethanol (0.1% v/v), or; (C) acetate (0.1% w/v as sodium acetate). Lane 1: 100 bp DNA ladder; Lane 2: PCR on cDNA reverse-transcribed from mRNA of strain SB2 grown on methane, ethanol, or acetate; Lane 3: PCR controls on mRNA extracted from strain SB2; Lane 4: negative control ($ddH_2O$). Arrow indicates size of expected PCR product. RNA was extracted following previously developed procedures with minor modifications (Han and Semrau, 2004). Organisms were collected after 72 hours ($OD_{600}$=0.45), 72 hours ($OD_{600}$=0.07), and 120 hours ($OD_{600}$=0.22) of growth on methane, ethanol, or acetate, respectively, by centrifugation at 12000 rpm for 5 min at 4° C. Organisms were then disrupted by six 30 s cycles of bead beating with being put on ice for 1 min in between each bead-beating cycle. RNA extraction was performed using QIAGEN RNeasy kit according to the manufacturer's instructions (QIAGEN, Valencia, Calif.). After being treated with RNase-free DNase I (Promega, Madison, Wis.) to remove any DNA contamination, DNase-treated RNA was purified using the Qiagen RNeasy kit according to the manufacturer's instructions (Valencia, Calif., USA). RNA was then reverse transcribed using SuperScript II reverse transcriptase with 250 ng of random primer (Invitrogen, Carlsbad, Calif.) according to the manufacturer's instructions (Invitrogen, Carlsbad, Calif.) to obtain cDNA. PCR amplification was then performed using pmoA specific primers A 189-mb661 (Costello & Lidstrom, 1999).
Figure 10:
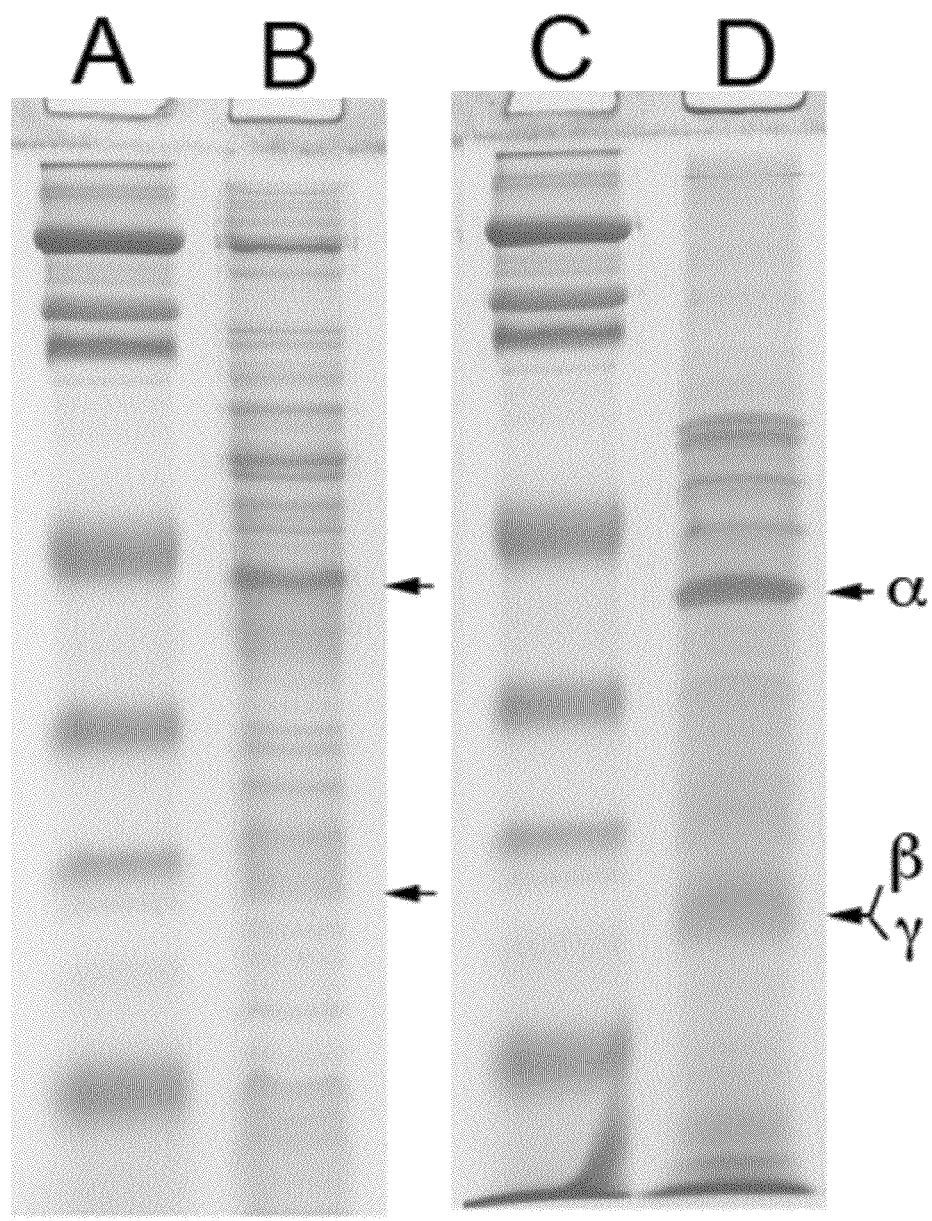
FIG. 10 shows SDS-polyacrylamide slab gel electrophoresis assays of whole-cell extracts of *Methylocystis* strain SB2 cultured on NMS medium with 5 µM copper and either 0.1% (w/v) acetate as sodium acetate (lane B) or 15% (v/v in the headspace) methane (lane D). SDS-PAGE was carried out by the Laemmli (1970) method on 12% gels. Gels were stained for total protein with Coomassie brilliant blue R. Polypeptides representing the expected molecular masses for the α, β, and γ subunits of the pMMO are marked. Lanes A and C represent molecular mass standards (204, 123, 80, 48, 34.3, 28.8, 20.7, 7.1 kDa). For growth of *Methylocystis* strain SB2 on either acetate or methane, the organism was first streaked onto NMS agar plates and incubated in the presence of methane, or streaked onto NMS agar plates with acetate. Inoculums were then taken to seed 50 ml of NMS medium with the same substrate. These cultures were then used to ultimately inoculate 500 ml of NMS medium with the same substrate.

Constitutive expression of pmoA: Previously, *Methylocystis* strain SB2 was found to be able to grow on methane, ethanol, and acetate (Example 1). Reverse transcription-polymerase chain reactions assays indicated that pmoA was expressed by strain SB2 when grown on either methane (FIG. 9, gel A), ethanol (FIG. 9, gel B), or acetate (FIG. 9, gel C) as the sole carbon and energy source, i.e., pmoA expression was constitutive with respect to carbon source. Confirmation of pMMO expression in both acetate and methane-grown cells was provided via SDS-PAGE gels (FIG. 10, lanes B and D, respectively).

This is in contrast to the earlier finding that *Methylocella silvestris* BL2$^T$ did not express sMMO (the only form of MMO it can express) when grown on acetate (Theisen, et al., 2005). It is known that the moderate acidophile *Methylocystis* strain H2s also constitutively expresses pMMO in the absence of methane and presence of acetate (Belova, et al., 2010) but to the best of our knowledge, similar information has not been presented for other acidophilic or mesophilic facultative methanotrophs, e.g., *Methylocapsa aurea* KYG$^T$, *Methylocystis heyeri* H2$^T$ or *Methylocystis echinoides* IMET10491$^T$.

Real-time PCR and qRT-PCR Analyses: Real-time quantitative RT-PCR was performed to confirm and quantify the expression of pMMO in *Methylocystis* strain SB2 growth as compared to cells grown with methane using the primers shown in Table 3.

TABLE 3

| Gene | Forward primer (5'-3') | Reverse primer (5'-3') | Amplicon length (bp) | TA (° C.) |
|---|---|---|---|---|
| 16S | AGTGGAACTGCGAGTGTAGAGGTG (SEQ ID NO: 3) | ACCAGGGTATCTAATCCTGTTTGCT (SEQ ID NO: 4) | 131 | 58 |
| pmoA | GGATCAACCGCTACGTCAACTTCT (SEQ ID NO: 5) | AGCCGAGCGAACCAACAATC (SEQ ID NO: 6) | 152 | 58 |

Figure 11:
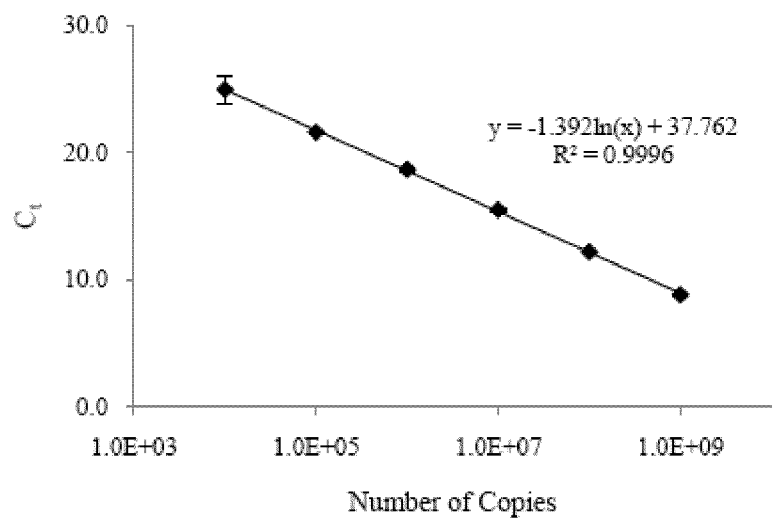
FIG. 11 shows standard calibration curves of 16S rRNA (A) and pmoA (B) amplification from *Methylocystis* strain SB2 for real time polymerase chain reaction and reverse transcription polymerase chain reaction assays.
Figure 11:
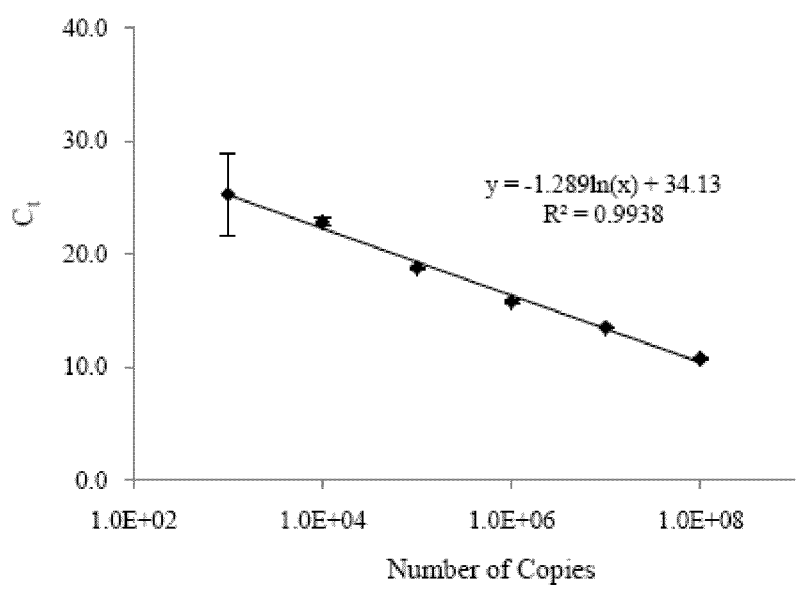

Specific primers were designed de novo from the partial 16S rRNA (GU734136 (SEQ ID NO: 1)) and pmoA (GU734137 (SEQ ID NO: 2)) sequences of *Methylocystis* strain SB2 using the Primer3 program (Rozen and Skaletsky, 2000). The forward and reverse primers (5'-3') for partial 16S rRNA gene amplification were as listed in Table 3, and were used to create an amplicon 131 bp in length. The forward and reverse primers (5'-3') for partial pmoA gene amplification were as listed in Table 3, and were used to create an amplicon 152 bp in length. 16s rRNA gene copy number and transcripts were calculated from measured $C_t$ values using a calibration curve based on five plasmid preparations with known 16S rRNA copy numbers ranging from $10^4$ to $10^9$ per microliter (FIG. 11A). Similarly, the copy numbers of pmoA gene copy number and transcripts were calculated from measured $C_t$ values using a calibration curve based on six plasmid preparations with known pmoA copy numbers ranging from $10^3$ to $10^8$ per microliter (FIG. 11B).

As shown in Table 4, the ratio of the copy number of 16S rRNA transcripts to 16S rRNA gene copy number remained relatively constant under most growth conditions, save for a two-fold decrease in the sample collected from strain SB2 grown to an $OD_{600}$ of 0.15 on acetate (significantly different at a 97% confidence interval from all other measurements).

for methane-grown organisms at two different cell densities. The same trend was found when the ratio of pmoA transcript number:pmoA gene copy number was normalized to overall rRNA transcript levels (last column of Table 4). Expression of pmoA, although measurable when *Methylocystis* strain SB2 was grown on acetate, was not constant, i.e., the quantity of pmoA transcript decreased eight-fold as strain SB2 was grown on acetate from an $OD_{600}$ of 0.11 to 0.15 significantly different at a 99% confidence interval). Normalization of pmoA expression to overall transcription activity reduced this difference to ~three-fold (significantly different at a 99% confidence interval). The pmoA transcript:pmoA gene copy number ratio was 15-100 fold lower in strain SB2 grown on acetate compared to when the strain was grown on methane (significant at a 99% confidence interval). A similar decrease in pmoA expression of acetate vs. methane-grown organisms was found when the ratio of pmoA transcript number:pmoA gene copy number was normalized to overall rRNA transcript levels (11-46 fold difference, significant at a 99% confidence interval). The copper-to-biomass ratio is known to regulate pmoA expression (Murrell et al., 2000), and it is possible, from the results presented here, positive regulation by methane may be another mechanism regulating the expression of pmoA in *Methylocystis* strain SB2. Such substrate stimulation of transcription has been observed for the expression of hydroxylamine oxidoreductase (HAO) genes in *Methylococcus capsulatus* Bath (Poret-Peterson et al., 2008).

TABLE 4

| Substrate | $OD_{600\,nm}$ | 16S transcript: 16S gene | pmoA transcript: pmoA gene | pmoA: 16S |
|---|---|---|---|---|
| $CH_4$ | 0.30 | 1410 (405)$^a$ | 2.88 (0.28) | $2.06 \times 10^{-3}$ ($6.23 \times 10^{-4}$) |
|  | 0.43 | 1680 (311) | 2.84 (0.64) | $1.69 \times 10^{-3}$ ($4.89 \times 10^{-4}$) |
| $CH_3COOH$ | 0.11 | 1270 (322) | $1.84 \times 10^{-1}$ ($2.78 \times 10^{-2}$) | $1.45 \times 10^{-4}$ ($4.28 \times 10^{-5}$) |
|  | 0.15 | 606 (129) | $2.71 \times 10^{-2}$ ($5.43 \times 10^{-3}$) | $4.48 \times 10^{-5}$ ($1.31 \times 10^{-5}$) |

Quantification of pmoA expression in *Methylocystis* strain SB2 after growth on methane and acetate using real-time quantitative RT-PCR. Cell pellets were collected from *Methylocystis* sp. SB2 grown on methane (1:1 methane-to-air ratio) or acetate (0.1% w/v) in nitrate mineral salt (NMS) medium (Whittenbury et al., 1970). Genomic DNA was prepared from these samples by lysing the pellets by bead beating (Han and Semrau, 2004) followed by three freeze-thaw cycles. (Dedysh et al., 1998). The final DNA samples were then collected in 50 µl distilled-deionized water. Total RNA was extracted from 1.5 ml of culture samples as described by Han and Semrau (2004). The final RNA samples were then collected in 36 µl distilled-deionized water. Real-time quantitative PCR and RT-PCR was performed in triplicate using RealMasterMix SYBR ROX solution (5 Prime, Gaithersburg, MD) with the original primer sets targeting 16S rRNA and pmoA (Table 3). A three-step cycle with an initial denaturation step was used for assays with both 16S rRNA and pmoA genes: initial denaturation at 94° C. for two minutes and 40 cycles of denaturation (94° C. for 15 s), annealing (58° C. for 20 s), and extension (68° C. for 30 sec). The raw copy number data were adjusted for the different final dilutions of DNA and RNA prior to real time PCR and RT-PCR. The standard deviation reported in parentheses were calculated using propagation of error, and are predominantly due to variability in biological replicates and not from instrument sensitivity.

This suggests that *Methylocystis* strain SB2 activity may be reduced as the organism approaches the stationary phase when grown on acetate while the same trend does not happen when the organisms are grown on methane. At this time, it is not known why such a reduction in overall transcription activity occurred, but it is believed that acetate uptake dissipates the proton motive force (Axe and Bailey, 1995), possibly reducing cell activity over time.

Figure 12:
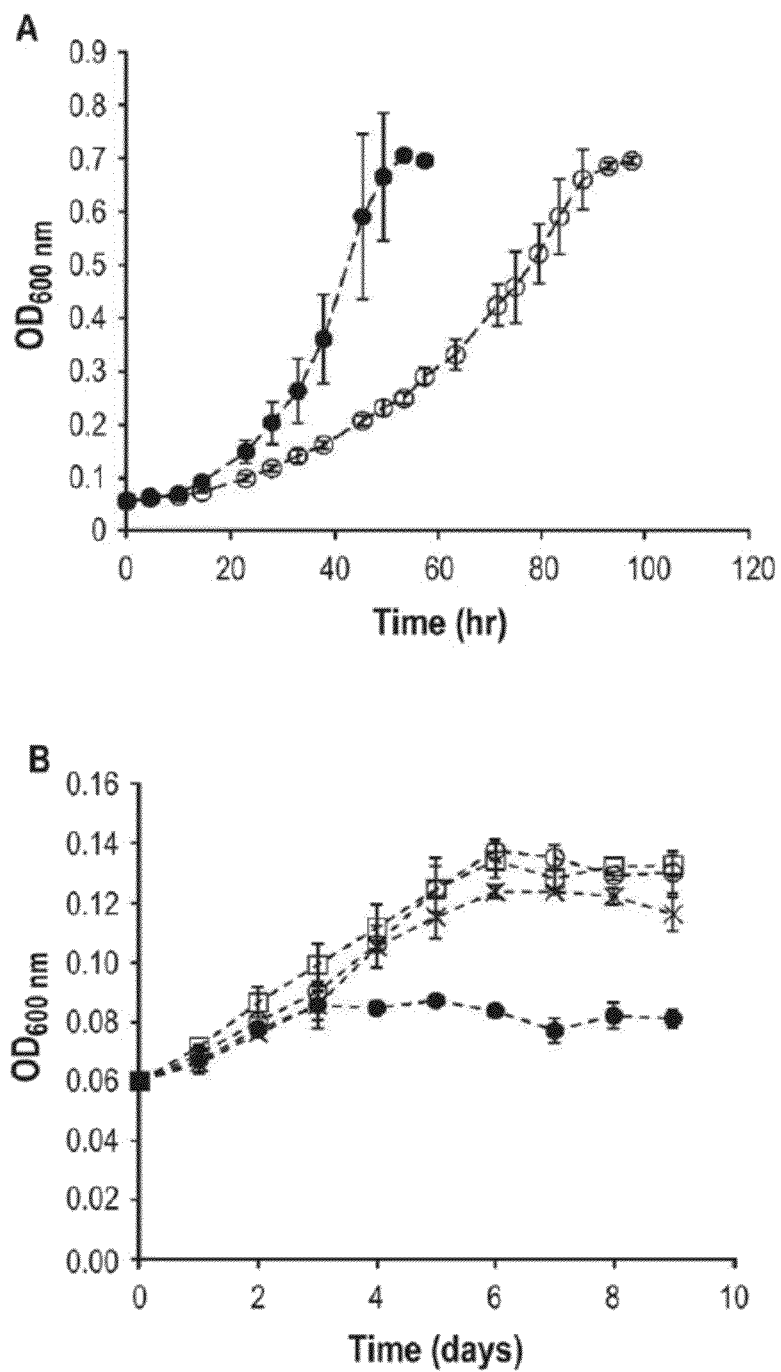
FIG. 12 represents the growth of *Methylocystis* strain SB2 solely on NMS medium with 10 µM copper and either (A) methane (15% v/v in the headspace) or (B) acetate (0.1% w/v as sodium acetate) in the presence/absence of equimolar concentrations (40 µM) of trichloroethylene (TCE), trans-dichloroethylene (t-DCE), and vinyl chloride (VC) and/or acetylene (1% v/v in the headspace). Symbols in (A): ●—methane only (positive control), ○—methane and 40 µM each of TCE, t-DCE, and VC. Symbols in (B): ○—acetate only (positive control), ●—acetate and 40 µM each of TCE, t-DCE, and VC, □—acetate, and acetylene, x—acetate, acetylene, and 40 µM each of TCE, t-DCE, and VC. *Methylocystis* strain SB2 was initially grown on methane (1:1 methane-to-air ratio) to the mid-exponential phase ($OD_{600}$ of 0.3-0.4 as measured using a Spectronic 20 spectrometer (Milton Roy Company, USA)). Before transferring for growth on either acetate or methane, the flasks were flushed 10 times with air and allowed to equilibrate after each flushing to eliminate any methane dissolved in the medium. The cultures were then diluted to an $OD_{600}$ of 0.06 with fresh NMS medium. Five ml aliquots were added to serum vials specially fabricated to measure growth as $OD_{600}$ over time and respective growth substrates were added. For addition of methane, 5 ml of headspace was replaced with >99.99% methane after sealing the vials for a final concentration of 15% v/v in the headspace. For addition of acetate, sodium acetate stock solution was pipetted for a final concentration of 0.1% (w/v) before sealing. Growth was monitored by measuring absorbance at 600 nm ($OD_{600}$). Bars indicate the range of duplicate samples.

Also as shown in Table 4, the ratio of pmoA transcript to the copy number of pmoA in chromosomal DNA was constant Growth and chlorinated ethene degradation: When grown on methane, growth of *Methylocystis* strain SB2 was reduced in the presence of an equimolar mixture of TCE, t-DCE, and VC (FIG. 12A). In the absence of chlorinated ethenes, the specific growth rate was 0.057 h$^{-1}$, and decreased to 0.03 h$^{-1}$ in the presence of 40 µM each of TCE, t-DCE, and VC. The maximum cell density, however, was unaffected by the addition TCE, t-DCE, and VC. After 97.5 h of growth on methane at 30° C., *Methylocystis* strain SB2 completely degraded t-DCE and VC and removed ca. 40% of TCE (Table 5).

TABLE 5

| Substrates (s) | % Chlorinated ethene degraded (range of duplicate samples) | | | Time (hours) |
| --- | --- | --- | --- | --- |
| | TCE | t-DCE | VC | |
| $CH_4$ + TCE, t-DCE, and VC | 41 (11)[a] | 100 (0) | 100 (0) | 97.5 |
| $CH_3COOH$ + TCE, t-DCE, and VC | 6.5 (1) | 30 (3) | 30 (5) | 216 |
| $CH_3COOH$ + $C_2H_2$ + TCE, t-DCE, and VC | 3.3 (0) | 0 (0) | 0 (0) | 216 |
| Abiotic loss[a] | 5.2 (1) | 0 (0) | 1.8 (1) | 216 |

Degradation of chlorinated solvents by *Methylocystis* strain SB2 grown on methane or acetate in the presence or absence of acetylene. Measurements were taken with HP5890 Series II gas chromatograph as previously described by Lee et al. (2006).
[a]To measure any leakage and abiotic loss from the serum vials, negative controls were prepared by adding 40 µM of TCE, t-DCE, and VC to serum vials with 5 ml of sterile NMS medium.

This result was comparable to the previous results obtained with another type II methanotroph, *Methylosinus trichosporium* OB3b expressing pMMO where it was found that when 50 µM each of VC, t-DCE, and TCE was added, 97%, 98%, and 35% was degraded after 110 hours of growth on methane, respectively (Lee et al., 2006). When *Methylocystis* strain SB2 was grown on acetate with 10 µM copper, no inhibition of growth was observed during the initial phase of growth (0-72 h). Later, however, growth in the presence of chlorinated ethenes did not go beyond an $OD_{600}$ of ~0.08 (FIG. 12B). Although *Methylocystis* strain SB2 did not grow to high densities in the presence of these chlorinated ethenes, significant biodegradation of these compounds was observed, particularly t-DCE and VC. As can be seen in Table 5, ~30% of t-DCE and VC was removed during 216 hours of incubation. Removal of TCE, however, was not significantly distinguishable from abiotic losses.

Acetylene, a selective inhibitor of pMMO, was added to *Methylocystis* strain SB2 grown on acetate in the absence and presence of chlorinated ethenes to confirm that biodegradation was due to the presence of active pMMO. As can be seen in FIG. 12B, when acetylene was added to the headspace of the serum vials, the growth of *Methylocystis* strain SB2 was unaffected by the presence of the chlorinated ethenes. No degradation of chlorinated ethenes was observed, however, for these samples (Table 5), indicating that the degradation of t-DCE and VC in the absence of acetylene was due to active pMMO in *Methylocystis* strain SB2. Although VC and t-DCE were degraded by *Methylocystis* strain SB2 when grown on acetate in the absence of acetylene, as noted earlier, cell growth was inhibited. Collectively, these data provide evidence that the chlorinated ethenes themselves were not toxic at this concentration, but methanotrophic activity was inhibited by product(s) of chlorinated ethene oxidation as suggested earlier by Van Hylckama Vleig, et al., (1997).

Moreover, degradation of chlorinated hydrocarbon by *Methylocystis* strain SB2 grown on ethanol has been studied by the inventors of this disclosure, and the results have recently been published in J. Im & J. Semrau, (2011) *FEMS Microbiological Letters* 318: 137-142, which is hereby incorporated by reference in its entirety. The ability of *Methylocystis* strain SB2 to degrade chlorinated hydrocarbon, including trichloroethylene (TCE), trans-dichloroethylene (t-DCE), vinyl chloride (VC), 1,1,1-trichloroethane (1,1,1-TCA), dichloromethane (DCM), and chloroform (CF), was compared when *Methylocystis* strain SB2 was grown on ethanol relative to when it was grown with methane. Strain SB2 grown on methane degraded VC, t-DCE, TCE, 1,1,1-TCA, and CF, but not DCM. Growth of *Methylocystis* strain SB2 on methane was reduced in the presence of any chlorinated hydrocarbon mentioned above. *Methylocystis* strain SB2 grown on ethanol degraded VC, t-DCE, TCE, and 1,1,1-TCA, but not DCM or CF. With the exception of 1,1,1-TCA, the growth of strain SB2 on ethanol was not affected by any individual chlorinated hydrocarbon. No degradation of any chlorinated hydrocarbon was observed when acetylene was added to ethanol-grown *Methylocystis* strain SB2, indicating that this degradation was due to pMMO activity. When mixtures of chlorinated alkanes or alkenes were added to cultures growing on methane or ethanol, chlorinated alkene degradation occurred, but chlorinated alkanes were not, and growth was reduced on both methane and ethanol. Collectively, these data indicate that competitive inhibition of pMMO activity limits methanotrophic growth and pollutant degradation.

In summary, this study has revealed the expression of pmoA in a facultative methanotroph grown either on acetate or ethanol in the absence of methane, as well as active pMMO when grown on acetate. This information may be helpful in developing more effective in situ biodegradation strategies with methanotrophic bacteria. Knowing that at least some methanotrophs can grow and express active MMOs in the absence of methane, more sophisticated bioremediation strategies such as periodic addition of methane along with continuous addition of acetate (or ethanol) might prove promising alternatives. More research is needed to apply such facultative methanotrophs at the field scale. Developing means to assess the abundance of these organisms in situ, as well as finding ways to selectively stimulate the growth of these organisms while maintaining high levels of pMMO expression, are among the issues that need to be addressed.

The following methods were used for the studies described in Example 2.

Culture conditions *Methylocystis* strain SB2 was grown at 30° C. in 50 ml of nitrate mineral salt medium (Whittenbury et al., 1970) with 10 µM of copper added as $CuCl_2$ in 250-ml Erlenmeyer flasks shaken at 225 r.p.m. For methane-growth conditions, methane was added to the headspace to 1:1 methane-to-air ratio, and for acetate-growth conditions, sodium acetate was added to the final concentration of 1 mM, which was found to be the optimal concentration of acetate for *Methylocystis* strain SB2.

Chemicals Methane of highest-purity grade (>99.99%) was purchased from Airgas Company (Baltimore, Md.). Sodium acetate, ethanol (>99.5%), DCM (>99.5%) and TCE (>99.5%) were purchased from Fisher Scientific Company (Pittsburgh, Pa.). t-DCE (>98%), 1,1,1-TCA, and CF were purchased from Aldrich (Milwaukee, Wis.), and VC was purchased from Fluka (Ronkonkoma, N.Y.). Distilled deionized water (>18 mi2) was used for all experimental procedures. All glassware used in the experiments was washed thoroughly with detergents and acid-washed in 2 N $HNO_3$ overnight to remove trace metals including copper. Before use, the acid-washed glassware was rinsed four to five times with distilled deionized water to remove residual nitric acid.

Saturated stock solutions were prepared for TCE and t-DCE as described by Chang and Alvarez-Cohen (1996). Hamilton 1700 series gas-tight syringes (Hamilton, Reno, Nev.) were used to take aliquots from the stock solutions. Gaseous compounds, i.e., methane and VC, were transferred to gas bags before use. Aliquots were taken with Precision Lok gas-tight syringes purchased from Precision Sampling Corp (Baton Rouge, La.). The amount of chlorinated solvents to be added was calculated considering dimensionless Henry's constants at 30° C. Henry's constants for TCE, t-DCE, VC, 1,1,1-TCA, DCM, and CF at 30° C. were 0.458, 0.474, 1.262, 0.804, 0.125, and 0.189 (Morel and Hering, 1991; Tse et al., 1992; Gossett, 1987), respectively.

DNA and RNA Extraction $Methylocystis$ strain SB2 was initially grown on methane to the mid-exponential phase ($OD_{600}$ nm of 0.3-0.4). Cell suspensions were then flushed ten times with compressed air by vacuuming and refilling the gas in the headspace and diluted to $OD_{600,m}$<0.03 in 50 ml of fresh media in a 250-ml Erlenmeyer flask. Methane or acetate was then added as described above. These cells were grown to the late-exponential phase and 1.5 ml aliquots collected from each flask. The aliquots were pelleted by centrifugation at 12,000 rpm for 10 min and stored in −80° C.

Chromosomal DNA was extracted from these pellets by combining protocols used by Han and Semrau (2004) and Dedysh et al. (2005) to maximize extraction efficiency. Cell extraction buffer was prepared with hexadecyltrimethylammonium bromide (CTAB, Sigma, St. Louis, Mo.) as described by Dedysh et al (1998). 1 ml of cell extraction buffer and 500 g of 0.1 mm diameter zirconia/silica beads (BioSpec products, Bartlesville, Okla.) were added to the thawed pellets. Zirconia/silica beads were acid washed, rinsed with distilled deionized water, and oven-baked at 240° C. overnight prior to use. The cells were first lysed with bead beating in a Mini-Bead Beater (BioSpec products, Bartlesville, Okla.) at 4° C. six times for 30 s with 1 min interval in ice to avoid overheating of the samples (Han and Semrau, 2004). To increase the extraction efficiency, the cells then underwent three rapid freeze-and-thaw cycles by alternatively placing the cells in liquid nitrogen and a 65° C. water bath, making sure that the cells were completely frozen or thawed at each step (Dedysh et al., 1998). After the freeze-thaw cycles, Proteinase K (Sigma, St. Louis, Mo.) was added to the concentration of 50 pg/ml and the mixture vigorously mixed by vortexing. 100 μA of 20% sodium dodecyl sulfate (Sigma, St. Louis, Mo.) was then added and mixed by gently inverting the tubes five times (Dedysh et al., 2005). The mixture was then incubated at 65° C. for two hours with gentle inversions every 10-15 min. After settling the glass beads, 0.9 ml of the supernatant was carefully transferred to 2-ml Phase Lock Gel tubes (5 PRIME, Gaithersburg, Md.) for phenol-chloroform extraction (Dedysh et al., 2005).

For extraction of total RNA, cell pellets were lysed as described by Han and Semrau (2004). The QIAGEN RNeasy Mini Kit (QIAGEN, Valencia, Calif.) was used to extract total RNA from the lysates according to kit protocols. The extracted total RNA (30 lul) was treated with 3 gl of RNase-free DNase I (Promega, Madison, Wis.) at 37° C. for 30 min. The reaction was stopped by adding 3 μl of Stop Solution provided with DNase I and heating the solution at 65° C. for 10 min. PCR reactions were then performed targeting pmoil and 16S rRNA genes using A189/mb661 primers (Costello and Lidstrom, 1999) and 27f-1492r primers (Lane, 1991), respectively, on DNase treated total RNA samples to check for any DNA contamination. The reaction mixture for reverse transcription was prepared by adding 1 gl of 3 μg/μl random primers (Invitrogen, Carlsbad, Calif.) and 2 pl of 2.5 mM dNTP Mix (Invitrogen, Carlsbad, Calif.) to 9 pl of the RNA solution treated with DNase I. Reverse transcription was then performed using SuperScript II Reverse Transcriptase (Invitrogen, Carlsbad, Calif.) according to the manufacturer instructions.

The products of DNA and total RNA extractions were checked with PCR and two-step RT-PCR with A189/mb661 primers targeting pmoil before proceeding to real-time quantitative PCR and RT-PCR analyses. PCR and RT-PCR amplifications were performed with 50 pl of mixtures consisting of 5 μl of 10×PCR buffer, 1.5 pi of 50 mM $MgCl_2$, 1 μl of 1 mM dNTP mix, 20 pmoles of each primer, 2.5 units of Taq DNA polymerase (Invitrogen, Carlsbad, Calif.), and 50 ng of DNA template (Lee et al., 2009). Biometra TPersonal thermal cycler system (Labrepco Inc. Horsham, Pa.) was used with the following amplification program: denaturation at 94° C. for 3 min; 30 cycles of 94° C. for 30 s, 58° C. for 30 s, and 72° C. for 45 s; and a final extension at 72° C. for 5 min.

Real-time quantitative PCR and RT-PCR The primers for amplification of 16S rRNA and pmoA genes in the real-time quantitative PCR and RT-PCR analyses were designed de novo from the partial 16S rRNA (GU734136 (SEQ ID NO: 1)) and pmoA (GU734137 (SEQ ID NO: 2)) sequences of $Methylocystis$ strain SB2 using Primer3 program (Rozen and Skaletsky, 2000) to limit the amplicon length to less than 150 bp for more accurate quantification (Table 3). Real-time quantitative PCR assays were performed with RealMasterMix SYBR ROX solution (5 Prime, Gaithersburg, Md.) on a Mastercycler ep realplex apparatus (Eppendorf, Hamburg, Germany). PCR master mix was prepared by adding the forward and reverse primers to the final concentration of 0.2 mM in 1× RealMasterMix SYBR ROX solution prepared according to the instruction provided by the manufacturer. One microliter of genomic DNA or cDNA sample was added to 49 μl of PCR master mix pipetted into 96-well PCR plates (Eppendorf, Hamburg, Germany). For analysis of 16S rRNA, the cDNA samples were diluted by 100-fold, as the initial $C_t$ value was out of the range of the standard calibration curve. After all samples were loaded, the 96-well plate was sealed with heat sealing film (Eppendorf, Hamburg, Germany). A three-step cycle with an initial denaturation step was used for assays with both 16S rRNA and pmoA genes: initial denaturation at 94° C. for two minutes and 40 cycles of denaturation (94° C. for 15 s), annealing (58° C. for 20 s), and extension (68° C. for 30 s). All real-time quantitative PCR and RT-PCR analyses were done in triplicate. GraphPad Quickcals Software (GraphPad Software Inc., La Jolla, Calif.) was used for statistical comparison of the real-time PCR results.

To generate a calibration curve relating the threshold cycle ($C_t$) and the copy number of the target genes, dilution series of plasmid DNA with known copy number were prepared. 16S rRNA and pmoA genes were amplified with their respective primer sets (Table 2) from the genomic DNA extracted from $Methylocystis$ strain SB2.

The PCR products were then cloned with TOPO TA Cloning Kit (Invitrogen, Carlsbad, Calif.) into TOP10 ONESHOT competent cells (Invitrogen, Carlsbad, Calif.). The plasmids were extracted with QIAGEN Plasmid Mini Kit (QIAGEN, Valencia, Calif.). The copy numbers of these plasmids were calculated from nucleic acid concentrations measured with NanoDrop 1000 spectrometer (Thermo Scientific, Wilmington, Del.) and the molecular weight of the plasmids was provided by the manufacturer. Dilution series ranging from $10^9$ to $10^3$ copies per microliter were generated by serial dilution.

Growth and degradation of chlorinated solvents. The growth of $Methylocystis$ strain SB2 and degradation of the mixture of TCE, t-DCE, and VC were measured in three different conditions: methane, acetate, and acetate with acetylene (a selective inhibitor of both MMOs) (Prior and Dalton, 1985). The method used previously by Lee et al. (2006) and Yoon and Semrau (2008) was slightly modified for these assays. For all three growth conditions, *Methylocystis* strain SB2 was initially grown on methane to the mid-exponential phase ($OD_{600}$ nm of 0.3-0.4). This cell suspension was flushed with compressed air as described above to remove residual methane and diluted to $OD_{600}$<0.03 in 50 ml of fresh media in 250 ml Erlenmeyer flask. For growth on methane, methane was added to the headspace to an air:methane ratio of 1:1 and the cells were grown back to an $OD_{600}$ of ca. 0.06. After the flask was flushed with compressed air as described earlier, five milliliter aliquots were transferred to serum vials specially fabricated to measure growth at $OD_{600}$ over time as described earlier (Lee et al., 2006). Teflon-coated butyl-rubber stoppers (National Scientific Co., Duluth, Ga.) were used to seal the serum vials. After the serum vials were securely sealed, 5 ml of the air in headspace was replaced with 5 ml of methane to ensure sufficient methane for growth. For growth on acetate, 1 mM of sodium acetate (Im et al., 2010) instead of methane was added to the diluted cell suspension in 250-ml Erlenmeyer flasks. The cells were grown back up to an $OD_{600}$ of 0.06. After aliquots were transferred as described above, the serum vials were sealed without addition of any additional substrate. After sealed vials were prepared with added growth substrates, TCE, t-DCE, and VC were injected to the vials to yield an aqueous concentration of 40 μM for each compound. To a subset of serum vials for acetate-grown cells, 0.335 ml of acetylene was injected prior to the addition of chlorinated ethenes. To measure any leakage and abiotic loss from the serum vials, negative controls were prepared with 5 ml of sterile NMS medium (Yoon et al., 2008). All samples including negative controls were prepared in duplicate. The growth of *Methylocystis* strain SB2 was monitored until the cell growth was no longer observed. The initial and final concentration of TCE, t-DCE, and VC were measured with HP5890 Series II gas chromatograph equipped with a 75 m DB-624 column with 0.53 mm internal diameter (J&W Scientific Co.). One hundred microliters of headspace from each sample with chlorinated ethenes was manually injected with a Precision Lok gas-tight syringe. TCE and t-DCE were detected with an electron capture detector (ECD) with injector, oven, and detector temperatures set to 160, 120, and 250° C., respectively. VC was detected with a flame ionization detector (FID) with injector, oven, and detector temperatures set to 140, 120, and 250° C., respectively.

Example 3

A Method of Isolating a Metal-Binding Compound of the Present Disclosures from Culture Media of *Methylocystis* SB2

The initial copper concentration in the continuous batch reactors was 0.2 μM. Starter cultures for the batch reactors were grown in NMS containing 0.2 or 5 μM copper sulfate. A 10% percent inoculum is used for all fermentors and 80% of the media is removed when the optical density at 600 nm reached of 0.89±0.14, which generally takes 48-72 hours. After sample removal, fresh NMS media containing 0.2 μM Cu(II) can added to original volume and culture grown to the desired optical density. This process can be repeated every 48-72 hours depending on growth.

The metal-binding compound (also referred to herein as methanobactin (mb) or chalkophore) was separated from cells in the culture medium using a Centrimate™ PE tangential flow filtration system containing an OS030C10 centrimate filter cassette (Pall Corporation, Framingham, Mass.). The filtrate was loaded directly on a 5.0×30 cm Dianion HP20 (Sigma Chemical Co., St. Louis, Mo.). The metal-binding compound bound to the HP-20 column was washed with 3 column volumes of de-ionized $H_2O$, and eluted from the column using 60% acetylonitrile: 40% deionized $H_2O$, and freeze-dried.

All references, including publications, patent applications, and patents, cited herein are hereby incorporated by reference in here in their entirety to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Related Publications

The following listing provides the full citations of the publications referred to in Example 1.

Auman, A. J., Stolyar, S., Costello, A. M. and Lidstrom, M. E. (2000) Molecular characterization of methanotrophic isolates from freshwater lake sediment. *Appl Environ Microbiol* 66: 5259-5266.

Auman, A. J., Speake, C. C., and Lidstrom, M. E. (2001) nifH sequences and nitrogen fixation in type I and type II methanotrophs. Appl. Environ. Microbiol. 67: 4009-4016.

Axe, D. E. and Bailey, J. E. (1995) Transport of lactate and acetate through the energized cytoplasmic membrane of *Escherichia coli. Biotechnol Bioeng* 47: 8-19.

Belova, S. E., Baani, M. Suzina, N. E., Bodelier, P. L. E., Liesack, W., and Dedysh, S. N. (2010) Acetate utilization as a survival strategy of peat-inhabiting *Methylocystis* spp. *Environ Microbiol Rep.* DOI: 10.1111/j.1758-2229.2010.00180.x Best D. J. and Higgins I. J. (1981) Methane oxidizing activity and membrane morphology in methanol grown obligate methanotroph, *Methylosinus trichosporium* OB3b. *J Gen Microbiol* 125:73-84.

Bowman, J. P., Sly, L. I., Nichols, P. D., and Hayward, A. C. (1993) Revised taxonomy of the methanotrophs—description of Methylobacter gen-nov, emendation of *Methylococcus*, validation of *Methylosinus* and *Methylocystis* species, and a proposal that the family Methylococcaceae includes only the group-I methanotrophs. Intl J Syst Bacteriol 43: 735-753.

Brusseau, G. A., Tsien, H-C., Hanson, R. C., and Wackett, L. P. (1990) Optimization of trichloroethylene oxidation by methanotrophs and the use of a colorimetric assay to detect soluble methane monooxygenase activity. *Biodegradation* 1: 19-29.

Cashion, P., Holder-Franklin, M. A., McCully, J. and Franklin, M. (1977) A rapid method for the base ratio determination of bacterial DNA. *Anal Biochem* 81: 461-466.

Cornish, A., Nicholis, K. M, Scott, D., Hunter, B. K., Aston, W. J., Higgins, I. J. and Sanders. K. M. (1984) In vivo $^{13}C$ NMR investigations of methanol oxidation by the obligate methanotroph *Methylosinus trichosporium* OB3b. *J Gen Microbiol* 130: 2564-2575.

Costello, A. M., and Lidstrom, M. E. (1999) Molecular characterization of functional and phylogenetic genes from natural populations of methanotrophs in lake sediments. *Appl Environ Microbiol* 65: 5066-5074.

Dedysh S. N., Knief C. and Dunfield P. F. (2005) *Methylocella* species are facultatively methanotrophic. *J Bacteriol* 187: 4665-4670.

Dedysh, S. N., Liesack, W., Khmelenina, V. N., Suzina, N. E., Trotsenko, Y. A., Semrau, J. D., et al. (2000) *Methylocella palustris* gen nov., sp. nov. a new methane-oxidizing acidophilic bacterium from peat bogs, representing a novel subtype of serine pathway methanotrophs. *Int J Syst Evol Microbiol* 50: 955-969.

Dunfield, P. F., Belova, S. E., Vorob'ev A. V., Cornish, S. L., and Dedysh, S. N. (2010) *Methylocapsa aurea* sp. nov., a facultatively methanotrophic bacterium possessing a particulate methane monooxygenase. *Int J Syst Evol Microbiol* doi: 10.1099/ijs.0.020149-0.

Dunfield P. F., Yuryev A., Senin P., Smirnova A. V., Stott M. B., Hou S., et al. (2007) Methane oxidation by an extremely acidophilic bacterium of the phylum Verrucomicrobia. *Nature* 450: 879-883.

Dunfield P. F., Khmelenina V. N., Suzina N. E., Trotsenko Y. and Dedsyh S, N. (2003) *Methylocella silvestris* sp. nov., a novel methanotroph isolated from an acidic forest cambisol. *Int J Syst Evol Microbiol* 53: 1231-1239.

Hutchens, E., Radajewski, S., Dumont, M. G., McDonald, I. R., and Murrell, J. C. (2004) Analysis of methanotrophic bacteria in Movile Cave by stable isotope probing. *Environ Microbiol* 6: 111-120.

Islam T., Jensen S., Reigstad L. J., Larsen Ø. and Birkeland N-K. (2008) Methane oxidation at 55° C. and pH 2 by a thermoacidophilic bacterium belonging to the Verrucomicrobia phylum. *Proc Natl Acad Sci* 105: 300-304.

Jukes, T. H., and Cantor, C. R. (1969) Evolution of protein molecules. New York: Academic Press.

Leak, D. J. and Dalton, H. (1986) Growth yields of methanotrophs. *Appl Microbiol Biotechnol* 23: 477-481.

Li, H., Webb, S. P., Ivanic, J., and Jensen, J. H. (2004) Determinants of the relative reduction potentials of type-1 copper sites in proteins. *J. Am. Chem. Soc.* 126, 8010-8019.

Linton J. D. and Vokes J. (1978) Growth of the methane utilizing bacterium *Methylococcus* NCIB 11083 in mineral salts medium with methanol as a sole source of carbon. *FEMS Microbiol Lett* 4, 125-128.

Machonkin, T. E., Zhang, H. H., Hedman, B., Hodgson, K. O., and Solomon, E. I. (1998) Spectroscopic and magnetic studies of human ceruloplasmin: Identification of a redox-inactive reduced type 1 copper site. *Biochemistry* 37, 9570-9578.

McDonald, I. R., Kenna, E. M. and Murrell, J. C. (1995) Detection of methanotrophic bacteria in environmental samples with the PCR. *App Environ Microbiol* 61: 116-121.

Mesbah, M., Premachandran, U. and Whitman, W. (1989) Precise measurement of the G+C content of deoxyribonucleic acid by high performance liquid chromatography. *Int J Syst Bact* 39: 159-167.

Pol A., Heijmans K., Harhangi H. R., Tedesco D., Jetten M. S. M. and Op den Camp H. J. M. (2007) Methanotrophy below pH 1 by a new Verrucomicrobia species. *Nature* 450: 874-878.

Saitou, N. and Nei, M. (1987) The neighbor-joining method: a new method for reconstructing phylogenetic trees. *Mol Biol Evol* 4: 406-425.

Semrau, J. D., DiSpirito, A. A., and Yoon, S. (2010) Methanotrophs and copper. *FEMS Microbiol Rev.* 34: 496-531.

Tamaoka, J. and Komagata, K. (1984) Determination of DNA base composition by reversed-phase high-performance liquid chromatography. *FEMS Microbiol Lett* 25: 125-128.

Tamura, K., Dudley, J., Nei, M. and Kumar, S. (2007) MEGA4: molecular evolutionary genetics analysis (MEGA) software version 4.0. *Mol Biol Evol* 24: 1596-1599

Vela, G. R. and Wyss O. (1964) Improved stain for visualization of *Azotobacter* encystment. *J Bacteriol* 87: 476-477.

Wartiainen, I., Hestnes, A. G., McDonald, I. R. and Svenning, M. M. (2006) *Methylocystis rosea* sp. nov., a novel methanotrophic bacterium from Arctic wetland soil, Svalbard, Norway (78° N). *Intl J Syst Evol Microbiol* 56: 541-547.

Wayne, L. G., Brenner, D. J., Colwell, R. R., Grimont, P. A. D., Kandler, O., Krichevsky, M. I., et al. (1987) Report of the ad hoc committee on reconciliation of approaches to bacterial systematics. *Intl J Syst Bacteriol* 37: 463-464.

Whittenbury R, Phillips K. C., and Wilkinson J. G. (1970) Enrichment, isolation and some properties of methane-utilizing bacteria. *J Gen Microbiol* 61: 205-218.

Wilkinson T. G., Topiwara H. H., and Hamer G. (1974) Interactions in a mixed bacterial population growing on methane in continuous culture. *Biotechnol Bioengin* 16:41-59.

Yoon, S., Kraemer, S. M., DiSpirito, A. A., and Semrau J. D. (2010) An assay for screening microbial cultures for chalkophore production. *Environ Microbiol Rep* doi: 10.1111/j.1758-2229.2009.00125.x Zehr, J. P., and McReynolds, L. A. (1989) Use of degenerate oligonucleotides for amplification of the nifH gene from the marine cyanobacterium *Trichodesmium thiebautii*, *Appl Environ Microbiol* 55: 2522-2526.

The following listing provides the full citations of the publications referred to in Example 2.

Axe, D. E. and Bailey, J. E. (1995) Transport of lactate and acetate through the energized cytoplasmic membrane of *Escherichia coli. Biotechnol Bioeng* 47: 8-19.

Belova, S. E., Baani, M., Suzina, N. E., Bodelier, P. L. E., Liesack, W., Dedysh, S. N. Acetate utilization as a survival strategy of peat-inhabiting *Methylocystis* spp. *Environ Microbiol Rep. DOI:* 10.1111/j.1758-2229.2010.00180.x Choi, D. W., Kunz, R. C., Boyd, E. S., Semrau, J. D., Antholine, W. E., Han, J. I. et al. (2003) The membrane-associated methane monooxygenase (pMMO) and pMMO-NADH: quinone oxidoreductase complex from *Methylococcus capsulatus* Bath. *J Bacteriol* 185: 5755-5764.

Dedysh, S. N., Panikov, N. S., and Tiedje, J. M. (1998) Acidophilic methanotrophic communities from sphagnum peat bogs. *Appl Environ Microbiol* 64: 922-929.

Dedysh, S. N., Knief, C., and Dunfield, P. F. (2005) *Methylocella* species are facultatively methanotrophic. *J Bacteriol* 187: 4665-4670.

Dunfield, P. F., Khmelenina, V. N., Suzina, N. E., Trotsenko, Y. A., and Dedysh, S. N. (2003) *Methylocella silvestris* sp. nov., a novel methanotroph isolated from an acidic forest cambisol. *Int J Syst Evol Microbiol* 53: 1231-1239.

Dunfield, P. F., Belova, S. E., Vorob'ev, A. V., Cornish, S. L., and Dedysh, S. N. (2010) *Methylocapsa aurea* sp. nov., a facultatively methanotrophic bacterium possessing a particulate methane monooxygenase. *Int J Syst Evol Microbiol* DOI:ijs.0.020149-0

Fogel, M. M., Taddeo, A. R., and Fogel, S. (1986) Biodegradation of chlorinated ethenes by a methane-utilizing mixed culture. *Appl Environ Microbiol* 51: 720-724.

Gossett J. M. (1987) Measurement of Henry's law constants for C1 and C2 chlorinated hydrocarbons. *Environ Sci Technol* 21: 202-208.

Han, J. I., and Semrau, J. D. (2004) Quantification of gene expression in methanotrophs by competitive reverse transcription-polymerase chain reaction. *Environ Microbiol* 6: 388-399.

Hanson, R. S., and Hanson, T. S. (1996) Methanotrophic bacteria. *Microbiol Rev* 60:439-471.

Laemmli, U. K. (1970) Cleavage of structural proteins during the assembly of the head of bacteriophage T4. *Nature* 227:680-685.

Im, J., Lee, S-W., Yoon, S., DiSpirito, A. A. and Semrau, J. D. (2010). Characterization of a novel facultative *Methylocystis* species capable of growth on methane, ethanol, and acetate. Submitted, *Env Microbio Rep.*

Jukes-Cantor correction, Jukes-Cantor, 1969. Evolution of protein molecules. New York: Academic Press.

Lee, S. W., Keeney, D. R., Lim, D. H., Dispirito, A. A., and Semrau, J. D. (2006) Mixed pollutant degradation by *Methylosinus trichosporium* OB3b expressing either soluble or particulate methane monooxygenase: can the tortoise beat the hare? *Appl Environ Microbiol* 72: 7503-7509.

Maymo-Gatell, X., Anguish, T., and Zinder, S. H. (1999) Reductive dechlorination of chlorinated ethenes and 1,2-dichloroethane by "*Dehalococcoides ethenogenes*" 195. *Appl Environ Microbiol* 65: 3108-3113.

Morton, J. D., Hayes, K. F., and Semrau, J. D. (2000) Effect of copper speciation on whole-cell soluble methane monooxygenase activity in *Methylosinus trichosporium* OB3b. *Appl Environ Microbiol* 66: 1730-1733.

Murrell, J. C., McDonald, I. R., and Gilbert, B. (2000) Regulation of expression of methane monooxygenases by copper ions. *Trends Microbiol* 8: 221-225.

Nielsen, A. K., Gerdes, K., and Murrell, J. C. (1997) Copper-dependent reciprocal transcriptional regulation of methane monooxygenase genes in *Methylococcus capsulatus* and *Methylosinus trichosporium*. *Mol Microbiol* 25: 399-409.

Oldenhuis, R., Vink, R. L., Janssen, D. B., and Witholt, B. (1989) Degradation of chlorinated aliphatic hydrocarbons by *Methylosinus trichosporium* OB3b expressing soluble methane monooxygenase. *Appl Environ Microbiol* 55: 2819-2826.

Poret-Peterson, A. T., Graham, J. E., Gulledge, J., and Klotz, M. G. (2008) Transcription of nitrification genes by the methane-oxidizing bacterium, *Methylococcus capsulatus* strain Bath. *ISME J* 2: 1213-1220.

Prior, S. D., and Dalton, H. (1985) The effect of copper ions on membrane content and methane monooxygenase activity in methanol-grown cells of *Methylococcus capsulatus* (Bath). *J Gen Microbiol* 131: 155-163.

Rozen, S. and Skaletsky, H. (2000) Primer3 on the WWW for general users and for biologist programmers. In Bioinformatics Methods and Protocols: Methods in Molecular Biology. Krawetz, S., Misener, S. (eds). Totowa, N.J., USA: Humana Press, pp 365-386.

Saitou and Nei. (1987) *Mol Biol Evol* 4:406-425.

Scheutz, C., Mosbaek, H., and Kjeldsen, P. (2004) Attenuation of methane and volatile organic compounds in landfill soil covers. *J Environ Qual* 33: 61-71.

Semprini, L., Roberts, P. V., Hopkins, G. D., McCarty, P. L. (1990) A field evaluation of in-situ biodegradation of chlorinated ethenes: part 2, results of biostimulation and biotransformation experiments. *Ground Wat* 28:715-727.

Semrau, J. D., DiSpirito, A. A., and Yoon, S. (2010) Methanotrophs and copper. *FEMS Microbiol Rev* 34: 496-531.

Tamura et al. (2007) *Mol Biol Evol* 24:1596-1599

Tsien, H. C., Brusseau, G. A., Hanson, R. S., and Waclett, L. P. (1989) Biodegradation of trichloroethylene by *Methylosinus trichosporium* OB3b. *Appl Environ Microbiol* 55: 3155-3161.

Van Hylckama Vlieg, J. E. T., de Koning, W., and Janssen, D. B. (1996) Transformation kinetics of chlorinated ethenes by *Methylosinus trichosporium* OB3b and detection of unstable epoxides by on-line gas chromatography. *Appl Environ Microbiol* 62: 3304-3312.

Van Hylckama Vlieg, J. E. T., De Koning, W., and Janssen, D. B. (1997) Effect of chlorinated ethene conversion on viability and activity of *Methylosinus trichosporium* OB3b. Appl Environ Microbiol 63: 4961-4964.

Whittenbury, R., Phillips, K. C., and Wilkinson, J. F. (1970) Enrichment, isolation and some properties of methane-utilizing bacteria. *J Gen Microbiol* 61: 205-218.

Yoon, S, and Semrau, J. D. (2008) Measurement and modeling of multiple substrate oxidation by methanotrophs at 20° C. *FEMS Microbiol Lett* 287: 156-162.

We claim:

1. An isolated or purified compound having a molecular weight of less than 1 kDa and comprising at least four amino acids, a first metal binding moiety comprising a substituted imidazolone ring ($M_1$), and a second metal binding moiety comprising a substituted oxazolone ring ($M_2$), wherein $M_1$ and $M_2$ are linked by a dipeptide, and wherein $M_1$ and $M_2$ bind to a single metal atom.

2. The isolated or purified compound of claim 1 comprising the structure of Formula I:

$$M_1\text{-}P_1\text{-}M_2\text{-}P_2 \qquad \text{[Formula I]}$$

wherein $P_1$ is the dipeptide linking $M_1$ and $M_2$, $P_2$ is a peptide comprising at least two amino acids, $M_1$ is the first metal binding moiety comprising a substituted imidazolone ring, and $M_2$ is the second metal binding moiety-comprising a substituted oxazolone ring.

3. The isolated or purified compound of claim 2, wherein $P_2$ is a dipeptide or tripeptide.

4. The isolated or purified compound of claim 2, wherein $M_1$ comprises a structure of Formula IIa:

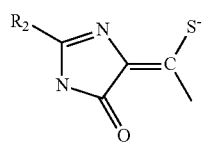

[Formula IIa]

wherein $R_2$ comprises a side chain along with the backbone alpha-carbon of an amino acid.

5. The isolated or purified compound of claim 2, wherein $M_2$ comprises a structure of Formula IIb:

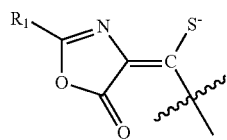

[Formula IIb]

wherein $R_1$ comprises a side chain along with the backbone nitrogen and alpha-carbon atoms of an amino acid.

6. The isolated or purified compound of claim 4, wherein $M_2$ comprises the structure of Formula IIb:

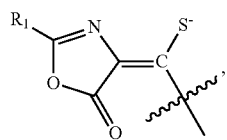

[Formula IIb]

wherein $R_1$ comprises a side chain along with the backbone nitrogen and alpha-carbon atoms of a naturally-occurring amino acid, and wherein $R_2$ comprises a side chain along with the alpha-carbon of a naturally-occurring amino acid, which is converted to an oxo group.

7. The isolated or purified compound of claim 4, wherein $M_2$ comprises the structure of Formula IIb:

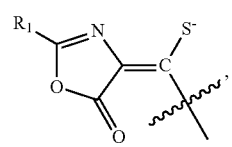

[Formula IIb]

wherein $R_1$ comprises a side chain along with the backbone nitrogen and alpha-carbon atoms of a non-coded amino acid, wherein $R_2$ comprises a side chain of a non-coded amino acid, or wherein each of $R_1$ and $R_2$ comprises a side chain along with the alpha-carbon atom, which has been converted to an oxo group, of a non-coded amino acid.

8. The isolated or purified compound of claim 4, wherein $M_2$ comprises the structure of Formula IIb:

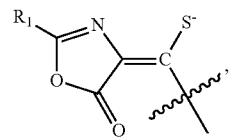

[Formula IIb]

wherein $R_1$ of Formula IIb comprises a structure of Formula III, wherein Formula III is attached as R1 to the structure of Formula IIb at the indicated attachment point:

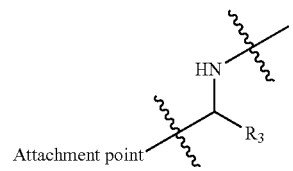

[Formula III]

and wherein $R_3$ is a hydroxyalkyl or an alkylated sulfate.

9. The isolated or purified compound of claim 8, wherein the hydroxylalkyl is —$CH(CH_3)OH$.

10. The isolated or purified compound of claim 8, wherein the alkylated sulfate is a C1 to C4 sulfate.

11. The isolated or purified compound of claim 10, wherein the alkylated sulfate is —$CH(CH_3)SO_4^-$.

12. The isolated or purified compound of claim 4, wherein $R_2$ of Formula IIa comprises an alkylated guanidinium moiety.

13. The isolated or purified compound of claim 12, wherein $R_2$ of Formula IIa comprises a structure of Formula IV:

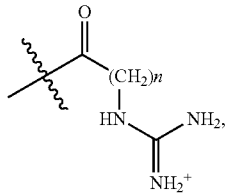

[Formula IV]

wherein n is an integer between 1 and 5.

14. The isolated or purified compound of claim 4, wherein $M_2$ comprises a structure of Formula IIb

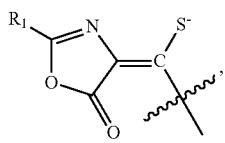

[Formula IIb]

wherein $R_1$ comprises a structure of Formula III:

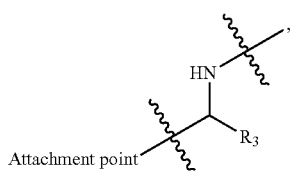

[Formula III]

wherein $R_3$ is a hydroxyalkyl or an alkylated sulfate.

15. The isolated or purified compound of claim 4, wherein $M_1$ comprises a structure of Formula IIa, wherein $R_2$ comprises a structure of Formula IV:

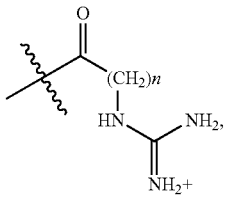

[Formula IV]

wherein n is an integer between 1 and 5.

16. The isolated or purified compound of claim 1, wherein $M_1$ and $M_2$ bind to a single metal atom selected from the group consisting of Au(III), Cd(II), Co(II), Cr(VI), Cu(I), Cu(II), Fe(II), Fe(III), Hg(I), Hg(II), Ni(II), Zn(II), Ag(I), Pb(II), Pb(IV), Al(III), Mn(II), Mn(III), Mn(IV), Mn(VI), Mn(VII), U(IV), and U(VI), or a combination thereof.

17. The isolated or purified compound of claim 16, wherein $M_1$ and $M_2$ preferentially bind to copper.

18. The isolated or purified compound of claim 2, wherein $P_2$ comprises a structure of $aa_3$-$aa_4$ or $aa_3$-$aa_4$-$aa_5$, wherein each of $aa_3$, $aa_4$ and $aa_5$ is a small aliphatic amino acid.

19. The isolated or purified compound of claim 2, wherein $P_1$ comprises a structure of $aa_1$-$aa_2$, wherein $aa_2$ is a sulfur-containing amino acid or a hydroxyl-containing amino acid and $aa_1$ is a small aliphatic amino acid.

20. The isolated or purified compound of claim 18, wherein the small aliphatic amino acid is selected from the group consisting of Ala, Gly, Ser, Thr, and Pro.

21. The isolated or purified compound of claim 20, wherein each of $aa_3$, and $aa_4$ is Ala, and $aa_5$ is Thr.

22. The isolated or purified compound of claim 19, wherein $aa_2$ is Ser or cysteic acid.

23. The isolated or purified compound of claim 1, comprising one of the following structures when bound to a single metal atom:

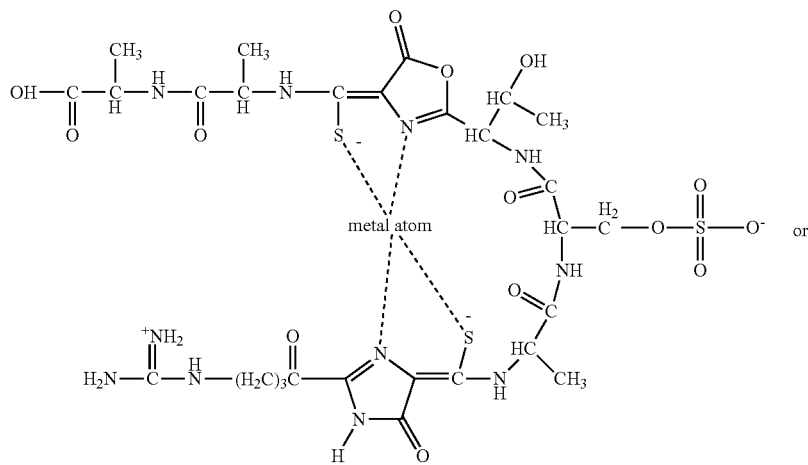

-continued

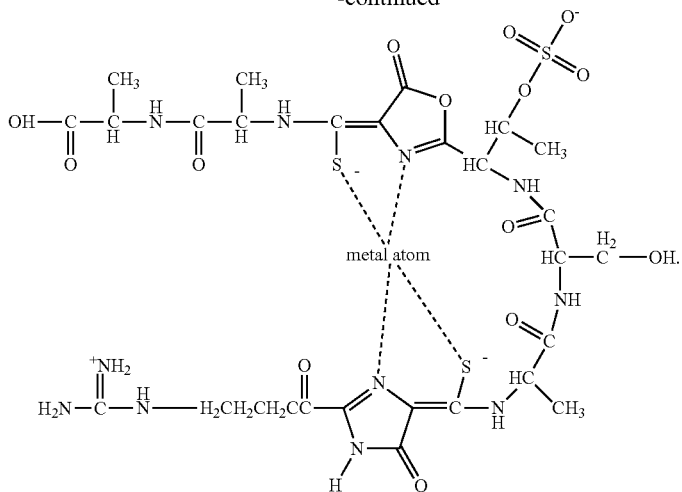

24. An isolated or purified complex comprising the compound in accordance with claim 1, wherein $M_1$ and $M_2$ are bound to a single metal atom.

25. The isolated or purified complex of claim 24, wherein the metal atom is selected from the group consisting of: Au(III), Cd(II), Co(II), Cr(VI), Cu(I), Cu(II), Fe(II), Fe(III), Hg(I), Hg(II), Ni(II), Zn(II), Ag(I), Pb(II), Pb(IV), Al(III), Mn(II), Mn(III), Mn(IV), Mn(VI), Mn(VII), U(IV), and U(VI) or a combination thereof.

26. The isolated or purified compound of claim 25, wherein the metal atom is Cu(I).

27. A conjugate comprising a compound of claim 1 linked to a heterologous moiety.

28. The conjugate of claim 27, wherein the heterologous moiety is an amino acid or peptide linked to the compound via a peptide bond.

29. The conjugate of claim 27, wherein the heterologous moiety is a polymer.

30. A method of reducing the concentration of a metal atom from a liquid system, comprising contacting the system with the compound of claim 1, to form complexes comprising the compound bound to the metal atom form in the system, and removing the complexes from the system.

31. The method of claim 30, wherein the metal is selected from the group consisting of: Au(III), Cd(II), Co(II), Cr(VI), Cu(I), Cu(II), Fe(II), Fe(III), Hg(I), Hg(II), Ni(II), Zn(II), Ag(I), Pb(II), Pb(IV), ARM), Mn(II), Mn(III), Mn(IV), Mn(VI), Mn(VII), U(IV), and U(VI), or a combination thereof.

32. The method of claim 31, wherein the metal is mercury.

33. A method of producing the complex of claim 24 comprising a metal atom, comprising incubating a solution comprising a metal atom with the compound of claim 1.

34. The method of claim 33, wherein the metal atom is gold, rhodium, platinum, or palladium.

\* \* \* \* \*